US009375542B2

(12) United States Patent
Doyle et al.

(10) Patent No.: US 9,375,542 B2
(45) Date of Patent: Jun. 28, 2016

(54) SYSTEMS AND METHODS FOR MONITORING, MANAGING, AND/OR PREVENTING FATIGUE DURING VENTILATION

(71) Applicant: Covidien LP, Mansfield, MA (US)

(72) Inventors: Peter Doyle, Vista, CA (US); Gardner Kimm, Carlsbad, CA (US); Phyllis Angelico, Carlsbad, CA (US)

(73) Assignee: COVIDIEN LP, Mansfield, MA (US)

( * ) Notice: Subject to any disclaimer, the term of this patent is extended or adjusted under 35 U.S.C. 154(b) by 484 days.

(21) Appl. No.: 13/671,815

(22) Filed: Nov. 8, 2012

(65) Prior Publication Data

US 2014/0123979 A1 May 8, 2014

(51) Int. Cl.
*A61M 11/00* (2006.01)
*A61M 16/00* (2006.01)

(52) U.S. Cl.
CPC ... *A61M 16/0057* (2013.01); *A61M 2016/0021* (2013.01); *A61M 2016/0027* (2013.01); *A61M 2016/0039* (2013.01); *A61M 2202/0208* (2013.01); *A61M 2205/502* (2013.01); *A61M 2205/505* (2013.01); *A61M 2205/52* (2013.01); *A61M 2230/435* (2013.01); *A61M 2230/60* (2013.01)

(58) Field of Classification Search
CPC ............... A61M 16/0051; A61M 16/0003; A61M 16/0069; A61M 2205/502; A61M 16/0057; A61M 2016/0021; A61M 2016/0027; A61M 2016/0039; A61M 2202/0208; A61M 2205/505; A61M 2205/52; A61M 2230/435; A61M 2230/60

USPC ............... 128/204.18, 204.21–204.23
See application file for complete search history.

(56) References Cited

U.S. PATENT DOCUMENTS

| 4,127,123 | A | 11/1978 | Bird |
| 4,448,192 | A | 5/1984 | Stawitcke et al. |
| 4,527,557 | A | 7/1985 | DeVries et al. |
| 4,637,385 | A | 1/1987 | Rusz |
| 4,640,277 | A | 2/1987 | Meyer et al. |
| 4,655,213 | A | 4/1987 | Rapoport et al. |
| 4,752,089 | A | 6/1988 | Carter |
| 4,773,411 | A | 9/1988 | Downs |
| 4,805,612 | A | 2/1989 | Jensen |
| 4,805,613 | A | 2/1989 | Bird |
| 4,821,709 | A | 4/1989 | Jensen |

(Continued)

FOREIGN PATENT DOCUMENTS

| AT | 142112 | 9/1996 |
| CA | 2036184 | 11/1991 |

(Continued)

OTHER PUBLICATIONS

7200 Series Ventilator, Options, and Accessories: Operator's Manual. Nellcor Puritan Bennett, Part No. 22300 A, Sep. 1990, pp. 1-196.

(Continued)

*Primary Examiner* — Steven Douglas

(57) ABSTRACT

This disclosure describes systems and methods for determining patient fatigue during ventilation of a patient. The disclosure describes novel notification and/or management of patient fatigue during ventilation. Further, the disclosure describes system and methods for preventing diaphragm fatigue or weakness.

27 Claims, 6 Drawing Sheets

(56) References Cited

U.S. PATENT DOCUMENTS

| | | |
|---|---|---|
| 4,921,642 A | 5/1990 | LaTorraca |
| 4,954,799 A | 9/1990 | Kumar |
| 4,986,268 A | 1/1991 | Tehrani |
| 5,044,362 A | 9/1991 | Younes |
| 5,057,822 A | 10/1991 | Hoffman |
| 5,072,737 A | 12/1991 | Goulding |
| 5,107,830 A | 4/1992 | Younes |
| 5,148,802 A | 9/1992 | Sanders et al. |
| 5,150,291 A | 9/1992 | Cummings et al. |
| 5,161,525 A | 11/1992 | Kimm et al. |
| 5,165,398 A | 11/1992 | Bird |
| 5,237,987 A | 8/1993 | Anderson et al. |
| 5,239,995 A | 8/1993 | Estes et al. |
| 5,271,389 A | 12/1993 | Isaza et al. |
| 5,279,549 A | 1/1994 | Ranford |
| 5,299,568 A | 4/1994 | Forare et al. |
| 5,301,921 A | 4/1994 | Kumar |
| 5,307,795 A | 5/1994 | Whitwam et al. |
| 5,313,937 A | 5/1994 | Zdrojkowski |
| 5,319,540 A | 6/1994 | Isaza et al. |
| 5,325,861 A | 7/1994 | Goulding |
| 5,333,606 A | 8/1994 | Schneider et al. |
| 5,339,807 A | 8/1994 | Carter |
| 5,343,857 A | 9/1994 | Schneider et al. |
| 5,351,522 A | 10/1994 | Lura |
| 5,353,788 A | 10/1994 | Miles |
| 5,357,946 A | 10/1994 | Kee et al. |
| 5,368,019 A | 11/1994 | LaTorraca |
| 5,383,449 A | 1/1995 | Forare et al. |
| 5,385,142 A | 1/1995 | Brady et al. |
| 5,390,666 A | 2/1995 | Kimm et al. |
| 5,398,676 A | 3/1995 | Press et al. |
| 5,401,135 A | 3/1995 | Stoen et al. |
| 5,402,796 A | 4/1995 | Packer et al. |
| 5,407,174 A | 4/1995 | Kumar |
| 5,413,110 A | 5/1995 | Cummings et al. |
| 5,433,193 A | 7/1995 | Sanders et al. |
| 5,438,980 A | 8/1995 | Phillips |
| 5,443,075 A | 8/1995 | Holscher |
| 5,452,714 A | 9/1995 | Anderson et al. |
| 5,492,113 A | 2/1996 | Estes et al. |
| 5,507,282 A | 4/1996 | Younes |
| 5,513,631 A | 5/1996 | McWilliams |
| 5,517,983 A | 5/1996 | Deighan et al. |
| 5,520,071 A | 5/1996 | Jones |
| 5,524,615 A | 6/1996 | Power |
| RE35,295 E | 7/1996 | Estes et al. |
| 5,531,221 A | 7/1996 | Power |
| 5,535,738 A | 7/1996 | Estes et al. |
| 5,540,222 A | 7/1996 | Younes |
| 5,542,415 A | 8/1996 | Brody |
| 5,544,674 A | 8/1996 | Kelly |
| 5,549,106 A | 8/1996 | Gruenke et al. |
| 5,551,418 A | 9/1996 | Estes et al. |
| 5,572,993 A | 11/1996 | Kurome et al. |
| 5,582,163 A | 12/1996 | Bonassa |
| 5,596,984 A | 1/1997 | O'Mahoney et al. |
| 5,598,838 A | 2/1997 | Servidio et al. |
| 5,630,411 A | 5/1997 | Holscher |
| 5,632,269 A | 5/1997 | Zdrojkowski |
| 5,632,270 A | 5/1997 | O'Mahoney et al. |
| 5,645,048 A | 7/1997 | Brodsky et al. |
| 5,660,171 A | 8/1997 | Kimm et al. |
| 5,664,560 A | 9/1997 | Merrick et al. |
| 5,664,562 A | 9/1997 | Bourdon |
| 5,671,752 A | 9/1997 | Sinderby et al. |
| 5,671,767 A | 9/1997 | Kelly |
| 5,672,041 A | 9/1997 | Ringdahl et al. |
| 5,673,689 A | 10/1997 | Power |
| 5,692,497 A | 12/1997 | Schnitzer et al. |
| 5,694,923 A | 12/1997 | Hete et al. |
| 5,704,345 A | 1/1998 | Berthon-Jones |
| 5,715,812 A | 2/1998 | Deighan et al. |
| 5,720,278 A | 2/1998 | Lachmann et al. |
| 5,735,267 A | 4/1998 | Tobia |
| 5,743,253 A | 4/1998 | Castor et al. |
| 5,752,506 A | 5/1998 | Richardson |
| 5,762,480 A | 6/1998 | Adahan |
| 5,765,558 A | 6/1998 | Psaros et al. |
| 5,771,884 A | 6/1998 | Yarnall et al. |
| 5,782,233 A | 7/1998 | Niemi et al. |
| 5,791,339 A | 8/1998 | Winter |
| 5,794,615 A | 8/1998 | Estes |
| 5,794,986 A | 8/1998 | Gansel et al. |
| 5,803,065 A | 9/1998 | Zdrojkowski et al. |
| 5,813,399 A | 9/1998 | Isaza et al. |
| 5,823,187 A | 10/1998 | Estes et al. |
| 5,826,575 A | 10/1998 | Lall |
| 5,829,441 A | 11/1998 | Kidd et al. |
| 5,864,938 A | 2/1999 | Gansel et al. |
| 5,865,168 A | 2/1999 | Isaza |
| 5,868,133 A | 2/1999 | DeVries et al. |
| 5,878,744 A | 3/1999 | Pfeiffer |
| 5,881,717 A | 3/1999 | Isaza |
| 5,881,723 A | 3/1999 | Wallace et al. |
| 5,884,622 A | 3/1999 | Younes |
| 5,884,623 A | 3/1999 | Winter |
| 5,901,704 A | 5/1999 | Estes et al. |
| 5,904,141 A | 5/1999 | Estes et al. |
| 5,909,731 A | 6/1999 | O'Mahony et al. |
| 5,915,379 A | 6/1999 | Wallace et al. |
| 5,915,380 A | 6/1999 | Wallace et al. |
| 5,915,382 A | 6/1999 | Power |
| 5,918,597 A | 7/1999 | Jones et al. |
| 5,921,238 A | 7/1999 | Bourdon |
| 5,927,274 A | 7/1999 | Servidio et al. |
| 5,931,160 A | 8/1999 | Gilmore et al. |
| 5,934,274 A | 8/1999 | Merrick et al. |
| 5,957,130 A | 9/1999 | Krahbichler et al. |
| 5,970,975 A | 10/1999 | Estes et al. |
| 5,975,081 A | 11/1999 | Hood et al. |
| 6,024,089 A | 2/2000 | Wallace et al. |
| 6,029,664 A | 2/2000 | Zdrojkowski et al. |
| 6,029,665 A | 2/2000 | Berthon-Jones |
| 6,041,777 A | 3/2000 | Faithfull et al. |
| 6,041,780 A | 3/2000 | Richard et al. |
| 6,047,860 A | 4/2000 | Sanders |
| 6,076,523 A | 6/2000 | Jones et al. |
| 6,105,575 A | 8/2000 | Estes et al. |
| 6,116,240 A | 9/2000 | Merrick et al. |
| 6,116,464 A | 9/2000 | Sanders |
| 6,123,073 A | 9/2000 | Schlawin et al. |
| 6,135,105 A | 10/2000 | Lampotang et al. |
| 6,135,106 A | 10/2000 | Dirks et al. |
| 6,142,150 A | 11/2000 | O'Mahony et al. |
| 6,158,432 A | 12/2000 | Biondi et al. |
| 6,161,539 A | 12/2000 | Winter |
| 6,196,222 B1 | 3/2001 | Heinonen et al. |
| 6,209,540 B1 | 4/2001 | Sugiura et al. |
| 6,213,119 B1 | 4/2001 | Brydon et al. |
| 6,220,245 B1 | 4/2001 | Takabayashi et al. |
| 6,240,919 B1 | 6/2001 | MacDonald et al. |
| 6,253,765 B1 | 7/2001 | Hognelid et al. |
| 6,257,234 B1 | 7/2001 | Sun |
| 6,269,812 B1 | 8/2001 | Wallace et al. |
| 6,273,444 B1 | 8/2001 | Power |
| 6,283,119 B1 | 9/2001 | Bourdon |
| 6,302,105 B1 | 10/2001 | Wickham et al. |
| 6,302,851 B1 | 10/2001 | Gedeon |
| 6,305,372 B1 | 10/2001 | Servidio |
| 6,305,373 B1 | 10/2001 | Wallace et al. |
| 6,305,374 B1 | 10/2001 | Zdrojkowski et al. |
| 6,321,748 B1 | 11/2001 | O'Mahoney |
| 6,325,785 B1 | 12/2001 | Babkes et al. |
| 6,345,619 B1 | 2/2002 | Finn |
| 6,357,438 B1 | 3/2002 | Hansen |
| 6,360,745 B1 | 3/2002 | Wallace et al. |
| 6,369,838 B1 | 4/2002 | Wallace et al. |
| 6,371,113 B1 | 4/2002 | Tobia et al. |
| 6,371,114 B1 | 4/2002 | Schmidt et al. |
| 6,412,483 B1 | 7/2002 | Jones et al. |
| 6,427,689 B1 | 8/2002 | Estes et al. |
| 6,431,169 B1 | 8/2002 | do Val et al. |
| 6,439,229 B1 | 8/2002 | Du et al. |

(56) References Cited

U.S. PATENT DOCUMENTS

| | | |
|---|---|---|
| 6,463,930 B2 | 10/2002 | Biondi et al. |
| 6,467,477 B1 | 10/2002 | Frank et al. |
| 6,467,478 B1 | 10/2002 | Merrick et al. |
| 6,484,719 B1 | 11/2002 | Berthon-Jones |
| 6,526,970 B2 | 3/2003 | DeVries et al. |
| 6,532,956 B2 | 3/2003 | Hill |
| 6,532,957 B2 | 3/2003 | Berthon-Jones |
| 6,532,958 B1 | 3/2003 | Buan et al. |
| 6,539,940 B2 | 4/2003 | Zdrojkowski et al. |
| 6,546,930 B1 | 4/2003 | Emerson et al. |
| 6,553,991 B1 | 4/2003 | Isaza |
| 6,553,992 B1 | 4/2003 | Berthon-Jones et al. |
| 6,557,553 B1 | 5/2003 | Borrello |
| 6,557,554 B1 | 5/2003 | Sugiura |
| 6,561,187 B2 | 5/2003 | Schmidt et al. |
| 6,571,795 B2 | 6/2003 | Bourdon |
| 6,575,163 B1 | 6/2003 | Berthon-Jones |
| 6,578,575 B1 | 6/2003 | Jonson |
| 6,581,597 B2 | 6/2003 | Sugiura |
| 6,584,973 B1 | 7/2003 | Biondi et al. |
| 6,588,422 B1 | 7/2003 | Berthon-Jones et al. |
| 6,595,213 B2 | 7/2003 | Bennarsten |
| 6,609,517 B1 | 8/2003 | Estes et al. |
| 6,612,995 B2 | 9/2003 | Leonhardt et al. |
| 6,622,726 B1 | 9/2003 | Du |
| 6,626,175 B2 | 9/2003 | Jafari et al. |
| 6,629,527 B1 | 10/2003 | Estes et al. |
| 6,629,934 B2 | 10/2003 | Mault et al. |
| 6,631,716 B1 | 10/2003 | Robinson et al. |
| 6,640,806 B2 | 11/2003 | Yurko |
| 6,644,310 B1 | 11/2003 | Delache et al. |
| 6,651,657 B1 | 11/2003 | Manigel et al. |
| 6,668,824 B1 | 12/2003 | Isaza et al. |
| 6,668,829 B2 | 12/2003 | Biondi et al. |
| 6,672,300 B1 | 1/2004 | Grant |
| 6,675,797 B1 | 1/2004 | Berthon-Jones |
| 6,675,801 B2 | 1/2004 | Wallace et al. |
| 6,679,258 B1 | 1/2004 | Strom |
| 6,688,307 B2 | 2/2004 | Berthon-Jones |
| 6,708,691 B1 | 3/2004 | Hayek |
| 6,718,974 B1 | 4/2004 | Moberg |
| 6,725,447 B1 | 4/2004 | Gilman et al. |
| 6,739,337 B2 | 5/2004 | Isaza |
| 6,752,919 B2 | 6/2004 | Farha et al. |
| 6,755,193 B2 | 6/2004 | Berthon-Jones et al. |
| 6,758,217 B1 | 7/2004 | Younes |
| 6,761,167 B1 | 7/2004 | Nadjafizadeh et al. |
| 6,761,168 B1 | 7/2004 | Nadjafizadeh et al. |
| 6,796,305 B1 | 9/2004 | Banner et al. |
| 6,810,876 B2 | 11/2004 | Berthon-Jones |
| 6,814,074 B1 | 11/2004 | Nadjafizadeh et al. |
| 6,823,866 B2 | 11/2004 | Jafari et al. |
| 6,837,242 B2 | 1/2005 | Younes |
| 6,837,244 B2 | 1/2005 | Yagi et al. |
| 6,854,462 B2 | 2/2005 | Berthon-Jones et al. |
| 6,860,858 B2 | 3/2005 | Green et al. |
| 6,866,040 B1 | 3/2005 | Bourdon |
| 6,877,511 B2 | 4/2005 | DeVries et al. |
| 6,899,103 B1 | 5/2005 | Hood et al. |
| 6,909,912 B2 | 6/2005 | Melker |
| 6,910,480 B1 | 6/2005 | Berthon-Jones |
| 6,915,803 B2 | 7/2005 | Berthon-Jones et al. |
| 6,920,878 B2 | 7/2005 | Sinderby et al. |
| 6,932,084 B2 | 8/2005 | Estes et al. |
| 6,948,497 B2 | 9/2005 | Zdrojkowski et al. |
| 6,960,854 B2 | 11/2005 | Nadjafizadeh et al. |
| 6,976,487 B1 | 12/2005 | Melker et al. |
| 6,997,881 B2 | 2/2006 | Green et al. |
| 7,000,610 B2 | 2/2006 | Bennarsten et al. |
| 7,000,612 B2 | 2/2006 | Jafari et al. |
| 7,013,892 B2 | 3/2006 | Estes et al. |
| 7,017,574 B2 | 3/2006 | Biondi et al. |
| 7,021,310 B1 | 4/2006 | Sinderby et al. |
| 7,024,235 B2 | 4/2006 | Melker et al. |
| 7,032,589 B2 | 4/2006 | Kerechanin, II et al. |
| 7,036,504 B2 | 5/2006 | Wallace et al. |
| 7,040,321 B2 | 5/2006 | Gobel |
| 7,055,522 B2 | 6/2006 | Berthon-Jones |
| 7,066,173 B2 | 6/2006 | Banner et al. |
| 7,077,131 B2 | 7/2006 | Hansen |
| RE39,225 E | 8/2006 | Isaza et al. |
| 7,096,866 B2 | 8/2006 | Be'eri et al. |
| 7,100,607 B2 | 9/2006 | Zdrojkowski et al. |
| 7,100,609 B2 | 9/2006 | Berthon-Jones et al. |
| 7,117,438 B2 | 10/2006 | Wallace et al. |
| 7,127,278 B2 | 10/2006 | Melker et al. |
| 7,137,389 B2 | 11/2006 | Berthon-Jones |
| 7,152,598 B2 | 12/2006 | Morris et al. |
| 7,162,296 B2 | 1/2007 | Leonhardt et al. |
| 7,210,478 B2 | 5/2007 | Banner et al. |
| 7,225,013 B2 | 5/2007 | Geva et al. |
| 7,246,618 B2 | 7/2007 | Habashi |
| 7,255,103 B2 | 8/2007 | Bassin |
| 7,267,121 B2 | 9/2007 | Ivri |
| 7,270,126 B2 | 9/2007 | Wallace et al. |
| 7,270,128 B2 | 9/2007 | Berthon-Jones et al. |
| 7,296,573 B2 | 11/2007 | Estes et al. |
| 7,305,987 B2 | 12/2007 | Schöller et al. |
| 7,320,320 B2 | 1/2008 | Berthon-Jones |
| 7,331,343 B2 | 2/2008 | Schmidt et al. |
| 7,334,578 B2 | 2/2008 | Biondi et al. |
| 7,347,824 B2 | 3/2008 | Wilkinson et al. |
| 7,367,337 B2 | 5/2008 | Berthon-Jones et al. |
| 7,369,757 B2 | 5/2008 | Farbarik |
| 7,370,650 B2 | 5/2008 | Nadjafizadeh et al. |
| RE40,402 E | 6/2008 | Leonhardt et al. |
| 7,425,201 B2 | 9/2008 | Euliano et al. |
| 7,428,902 B2 | 9/2008 | Du et al. |
| 7,455,717 B2 | 11/2008 | Sprinkle |
| 7,460,959 B2 | 12/2008 | Jafari |
| 7,475,685 B2 | 1/2009 | Dietz et al. |
| 7,478,634 B2 | 1/2009 | Jam |
| 7,484,508 B2 | 2/2009 | Younes |
| 7,487,773 B2 | 2/2009 | Li |
| 7,509,957 B2 | 3/2009 | Duquette et al. |
| 7,516,742 B2 | 4/2009 | Stenzler et al. |
| 7,520,279 B2 | 4/2009 | Berthon-Jones |
| 7,533,670 B1 | 5/2009 | Freitag et al. |
| 7,556,038 B2 | 7/2009 | Kirby et al. |
| 7,562,657 B2 | 7/2009 | Blanch et al. |
| 7,588,031 B2 | 9/2009 | Truschel et al. |
| 7,610,914 B2 | 11/2009 | Bolam et al. |
| 7,617,824 B2 | 11/2009 | Doyle |
| 7,621,270 B2 | 11/2009 | Morris et al. |
| 7,621,271 B2 | 11/2009 | Brugnoli |
| 7,644,713 B2 | 1/2010 | Berthon-Jones |
| 7,654,802 B2 | 2/2010 | Crawford, Jr. et al. |
| 7,672,720 B2 | 3/2010 | Heath |
| 7,678,058 B2 | 3/2010 | Patangay et al. |
| 7,678,061 B2 | 3/2010 | Lee et al. |
| 7,682,312 B2 | 3/2010 | Lurie |
| 7,690,378 B1 | 4/2010 | Turcott |
| 7,694,677 B2 | 4/2010 | Tang |
| 7,697,990 B2 | 4/2010 | Ujhazy et al. |
| 7,708,016 B2 | 5/2010 | Zaiser et al. |
| 7,708,697 B2 | 5/2010 | Wilkinson et al. |
| 7,717,110 B2 | 5/2010 | Kane et al. |
| 7,717,111 B2 | 5/2010 | Schneider et al. |
| 7,717,113 B2 | 5/2010 | Andrieux |
| 7,722,546 B2 | 5/2010 | Madaus et al. |
| D618,356 S | 6/2010 | Ross |
| 7,727,160 B2 | 6/2010 | Green et al. |
| 7,730,886 B2 | 6/2010 | Berthon-Jones |
| 7,751,894 B1 | 7/2010 | Freeberg |
| 7,763,097 B2 | 7/2010 | Federspiel et al. |
| 7,770,578 B2 | 8/2010 | Estes et al. |
| 7,784,461 B2 | 8/2010 | Figueiredo et al. |
| 7,793,659 B2 | 9/2010 | Breen |
| 7,802,571 B2 | 9/2010 | Tehrani |
| 7,810,496 B2 | 10/2010 | Estes et al. |
| 7,810,497 B2 | 10/2010 | Pittman et al. |
| 7,814,906 B2 | 10/2010 | Moretti |
| 7,819,815 B2 | 10/2010 | Younes |
| 7,823,588 B2 | 11/2010 | Hansen |

(56) References Cited

U.S. PATENT DOCUMENTS

| | | |
|---|---|---|
| 7,849,854 B2 | 12/2010 | DeVries et al. |
| 7,855,716 B2 | 12/2010 | McCreary et al. |
| 7,866,318 B2 | 1/2011 | Bassin |
| 7,874,293 B2 | 1/2011 | Gunaratnam et al. |
| D632,796 S | 2/2011 | Ross et al. |
| D632,797 S | 2/2011 | Ross et al. |
| 7,891,354 B2 | 2/2011 | Farbarik |
| 7,893,560 B2 | 2/2011 | Carter |
| 7,914,459 B2 | 3/2011 | Green et al. |
| D638,852 S | 5/2011 | Skidmore et al. |
| 7,934,499 B2 | 5/2011 | Berthon-Jones |
| 7,984,714 B2 | 7/2011 | Hausmann et al. |
| D643,535 S | 8/2011 | Ross et al. |
| 7,992,557 B2 | 8/2011 | Nadjafizadeh et al. |
| 8,001,967 B2 | 8/2011 | Wallace et al. |
| D645,158 S | 9/2011 | Sanchez et al. |
| 8,021,310 B2 | 9/2011 | Sanborn et al. |
| D649,157 S | 11/2011 | Skidmore et al. |
| D652,521 S | 1/2012 | Ross et al. |
| D652,936 S | 1/2012 | Ross et al. |
| D653,749 S | 2/2012 | Winter et al. |
| 8,113,062 B2 | 2/2012 | Graboi et al. |
| D655,405 S | 3/2012 | Winter et al. |
| D655,809 S | 3/2012 | Winter et al. |
| D656,237 S | 3/2012 | Sanchez et al. |
| 8,181,648 B2 | 5/2012 | Perine et al. |
| 8,210,173 B2 | 7/2012 | Vandine |
| 8,210,174 B2 | 7/2012 | Farbarik |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 2002/0078958 A1 | 6/2002 | Stenzler |
| 2003/0000526 A1 | 1/2003 | Gobel |
| 2003/0010339 A1* | 1/2003 | Banner ............... A61M 16/00 128/204.18 |
| 2003/0062045 A1 | 4/2003 | Woodring et al. |
| 2003/0079750 A1 | 5/2003 | Berthon-Jones |
| 2003/0188748 A1 | 10/2003 | Sinderby et al. |
| 2005/0011519 A1 | 1/2005 | Sinderby et al. |
| 2005/0039748 A1 | 2/2005 | Andrieux |
| 2005/0139212 A1 | 6/2005 | Bourdon |
| 2006/0155336 A1 | 7/2006 | Heath |
| 2006/0174884 A1 | 8/2006 | Habashi |
| 2006/0235324 A1 | 10/2006 | Lynn |
| 2006/0249148 A1 | 11/2006 | Younes |
| 2006/0278223 A1 | 12/2006 | Younes |
| 2007/0000494 A1 | 1/2007 | Banner et al. |
| 2007/0017515 A1 | 1/2007 | Wallace et al. |
| 2007/0027375 A1 | 2/2007 | Melker et al. |
| 2007/0028921 A1 | 2/2007 | Banner et al. |
| 2007/0044796 A1 | 3/2007 | Zdrojkowski et al. |
| 2007/0044799 A1 | 3/2007 | Hete et al. |
| 2007/0077200 A1 | 4/2007 | Baker |
| 2007/0215146 A1 | 9/2007 | Douglas et al. |
| 2007/0221221 A1 | 9/2007 | Cook et al. |
| 2007/0227537 A1 | 10/2007 | Bemister et al. |
| 2007/0272241 A1 | 11/2007 | Sanborn et al. |
| 2007/0277823 A1 | 12/2007 | Al-Ali et al. |
| 2007/0284361 A1 | 12/2007 | Nadjafizadeh et al. |
| 2008/0011301 A1 | 1/2008 | Qian |
| 2008/0017198 A1 | 1/2008 | Ivri |
| 2008/0045813 A1 | 2/2008 | Phuah et al. |
| 2008/0053441 A1 | 3/2008 | Gottlib et al. |
| 2008/0053443 A1 | 3/2008 | Estes et al. |
| 2008/0053444 A1 | 3/2008 | Estes et al. |
| 2008/0072896 A1 | 3/2008 | Setzer et al. |
| 2008/0072901 A1 | 3/2008 | Habashi |
| 2008/0072902 A1 | 3/2008 | Setzer et al. |
| 2008/0078390 A1 | 4/2008 | Milne et al. |
| 2008/0083644 A1 | 4/2008 | Janbakhsh et al. |
| 2008/0092894 A1 | 4/2008 | Nicolazzi et al. |
| 2008/0097234 A1 | 4/2008 | Nicolazzi et al. |
| 2008/0110461 A1 | 5/2008 | Mulqueeny et al. |
| 2008/0121231 A1 | 5/2008 | Sinderby et al. |
| 2008/0142012 A1 | 6/2008 | Farnsworth et al. |
| 2008/0163872 A1 | 7/2008 | Negele et al. |
| 2008/0185002 A1 | 8/2008 | Berthon-Jones et al. |
| 2008/0196720 A1 | 8/2008 | Kollmeyer et al. |
| 2008/0202528 A1 | 8/2008 | Carter et al. |
| 2008/0216832 A1 | 9/2008 | Carter et al. |
| 2008/0216833 A1 | 9/2008 | Pujol et al. |
| 2008/0230065 A1 | 9/2008 | Heinonen |
| 2008/0234595 A1 | 9/2008 | Ranieri et al. |
| 2008/0236582 A1* | 10/2008 | Tehrani .................. 128/204.22 |
| 2008/0257349 A1 | 10/2008 | Hedner et al. |
| 2008/0283061 A1 | 11/2008 | Tiedje |
| 2008/0295839 A1 | 12/2008 | Habashi |
| 2009/0020120 A1 | 1/2009 | Schatzl et al. |
| 2009/0038616 A1 | 2/2009 | Mulcahy et al. |
| 2009/0056719 A1 | 3/2009 | Newman, Jr. |
| 2009/0084381 A1 | 4/2009 | DeVries et al. |
| 2009/0095298 A1 | 4/2009 | Gunaratnam et al. |
| 2009/0107502 A1 | 4/2009 | Younes |
| 2009/0114224 A1 | 5/2009 | Handzsuj et al. |
| 2009/0159082 A1 | 6/2009 | Eger |
| 2009/0165795 A1 | 7/2009 | Nadjafizadeh et al. |
| 2009/0171176 A1 | 7/2009 | Andersohn |
| 2009/0173347 A1 | 7/2009 | Berthon-Jones |
| 2009/0188502 A1 | 7/2009 | Tiedje |
| 2009/0199855 A1 | 8/2009 | Davenport |
| 2009/0205661 A1 | 8/2009 | Stephenson et al. |
| 2009/0205663 A1 | 8/2009 | Vandine et al. |
| 2009/0221926 A1 | 9/2009 | Younes |
| 2009/0229611 A1 | 9/2009 | Martin et al. |
| 2009/0241951 A1 | 10/2009 | Jafari et al. |
| 2009/0241952 A1 | 10/2009 | Nicolazzi et al. |
| 2009/0241953 A1 | 10/2009 | Vandine et al. |
| 2009/0241955 A1 | 10/2009 | Jafari et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0247891 A1 | 10/2009 | Wood |
| 2009/0301486 A1 | 12/2009 | Masic |
| 2009/0301487 A1 | 12/2009 | Masic |
| 2009/0301490 A1 | 12/2009 | Masic |
| 2009/0301491 A1 | 12/2009 | Masic et al. |
| 2010/0011307 A1 | 1/2010 | Desfossez et al. |
| 2010/0024820 A1 | 2/2010 | Bourdon |
| 2010/0051026 A1 | 3/2010 | Graboi |
| 2010/0051029 A1 | 3/2010 | Jafari et al. |
| 2010/0065055 A1 | 3/2010 | Morris et al. |
| 2010/0065057 A1 | 3/2010 | Berthon-Jones |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0078017 A1 | 4/2010 | Andrieux et al. |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0137380 A1 | 6/2010 | Maybaum |
| 2010/0137723 A1 | 6/2010 | Patangay et al. |
| 2010/0137729 A1 | 6/2010 | Pierry et al. |
| 2010/0137730 A1 | 6/2010 | Hatlestad |
| 2010/0139660 A1 | 6/2010 | Adahan |
| 2010/0145201 A1 | 6/2010 | Westbrook et al. |
| 2010/0147303 A1 | 6/2010 | Jafari et al. |
| 2010/0152553 A1 | 6/2010 | Ujhazy et al. |
| 2010/0152560 A1 | 6/2010 | Turcott |
| 2010/0170512 A1 | 7/2010 | Kuypers et al. |
| 2010/0174200 A1 | 7/2010 | Wood et al. |
| 2010/0174207 A1 | 7/2010 | Lee et al. |
| 2010/0180898 A1 | 7/2010 | Schneider et al. |
| 2010/0186741 A1 | 7/2010 | Aylsworth et al. |
| 2010/0186742 A1 | 7/2010 | Sherman et al. |
| 2010/0186743 A1 | 7/2010 | Kane et al. |
| 2010/0186744 A1 | 7/2010 | Andrieux |
| 2010/0191076 A1 | 7/2010 | Lewicke et al. |

(56) References Cited

U.S. PATENT DOCUMENTS

| | | |
|---|---|---|
| 2010/0191137 A1 | 7/2010 | Brada et al. |
| 2010/0192094 A1 | 7/2010 | Jeha et al. |
| 2010/0198086 A1 | 8/2010 | Kuo et al. |
| 2010/0199991 A1 | 8/2010 | Koledin |
| 2010/0210924 A1 | 8/2010 | Parthasarathy et al. |
| 2010/0218764 A1 | 9/2010 | Kwok et al. |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0218773 A1 | 9/2010 | Thornton |
| 2010/0222692 A1 | 9/2010 | McCawley et al. |
| 2010/0224190 A1 | 9/2010 | Tilley et al. |
| 2010/0228133 A1 | 9/2010 | Averina et al. |
| 2010/0228134 A1 | 9/2010 | Martikka et al. |
| 2010/0229863 A1 | 9/2010 | Enk |
| 2010/0234750 A1 | 9/2010 | Ariav et al. |
| 2010/0236553 A1 | 9/2010 | Jafari et al. |
| 2010/0236554 A1 | 9/2010 | Prete |
| 2010/0236555 A1 | 9/2010 | Jafari et al. |
| 2010/0241009 A1 | 9/2010 | Petkie |
| 2010/0242961 A1 | 9/2010 | Mougel et al. |
| 2010/0242965 A1 | 9/2010 | Berthon-Jones |
| 2010/0249630 A1 | 9/2010 | Droitcour et al. |
| 2010/0249631 A1 | 9/2010 | Aoki et al. |
| 2010/0249632 A1 | 9/2010 | Lee et al. |
| 2010/0249633 A1 | 9/2010 | Droitcour et al. |
| 2010/0252037 A1 | 10/2010 | Wondka et al. |
| 2010/0252039 A1 | 10/2010 | Cipollone et al. |
| 2010/0252040 A1 | 10/2010 | Kapust et al. |
| 2010/0252041 A1 | 10/2010 | Kapust et al. |
| 2010/0252042 A1 | 10/2010 | Kapust et al. |
| 2010/0252043 A1 | 10/2010 | Freitag |
| 2010/0256463 A1 | 10/2010 | Greenwald et al. |
| 2010/0258116 A1 | 10/2010 | Federspiel et al. |
| 2010/0258124 A1 | 10/2010 | Madaus et al. |
| 2010/0258126 A1 | 10/2010 | Ujhazy et al. |
| 2010/0258127 A1 | 10/2010 | Hk |
| 2010/0262032 A1 | 10/2010 | Freeberg |
| 2010/0275920 A1 | 11/2010 | Tham et al. |
| 2010/0282259 A1 | 11/2010 | Figueiredo et al. |
| 2010/0288279 A1 | 11/2010 | Seiver et al. |
| 2010/0288283 A1 | 11/2010 | Campbell et al. |
| 2010/0300446 A1 | 12/2010 | Nicolazzi et al. |
| 2011/0011400 A1 | 1/2011 | Gentner et al. |
| 2011/0017214 A1 | 1/2011 | Tehrani |
| 2011/0023878 A1 | 2/2011 | Thiessen |
| 2011/0023879 A1 | 2/2011 | Vandine et al. |
| 2011/0023880 A1 | 2/2011 | Thiessen |
| 2011/0023881 A1 | 2/2011 | Thiessen |
| 2011/0029910 A1 | 2/2011 | Thiessen |
| 2011/0036352 A1 | 2/2011 | Estes et al. |
| 2011/0041849 A1 | 2/2011 | Chen et al. |
| 2011/0041850 A1 | 2/2011 | Vandine et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0128008 A1 | 6/2011 | Carter |
| 2011/0132361 A1 | 6/2011 | Sanchez |
| 2011/0132362 A1 | 6/2011 | Sanchez |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0154241 A1 | 6/2011 | Skidmore et al. |
| 2011/0175728 A1 | 7/2011 | Baker, Jr. |
| 2011/0196251 A1 | 8/2011 | Jourdain et al. |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0230780 A1 | 9/2011 | Sanborn et al. |
| 2011/0249006 A1 | 10/2011 | Wallace et al. |
| 2011/0259330 A1 | 10/2011 | Jafari et al. |
| 2011/0259332 A1 | 10/2011 | Sanchez et al. |
| 2011/0259333 A1 | 10/2011 | Sanchez et al. |
| 2011/0265024 A1 | 10/2011 | Leone et al. |
| 2011/0271960 A1 | 11/2011 | Milne et al. |
| 2011/0273299 A1 | 11/2011 | Milne et al. |
| 2012/0000467 A1 | 1/2012 | Milne et al. |
| 2012/0000468 A1 | 1/2012 | Milne et al. |
| 2012/0000469 A1 | 1/2012 | Milne et al. |
| 2012/0000470 A1 | 1/2012 | Milne et al. |
| 2012/0029317 A1 | 2/2012 | Doyle et al. |
| 2012/0030611 A1 | 2/2012 | Skidmore |
| 2012/0060841 A1 | 3/2012 | Crawford, Jr. et al. |
| 2012/0071729 A1 | 3/2012 | Doyle et al. |
| 2012/0090611 A1 | 4/2012 | Graboi et al. |
| 2012/0096381 A1 | 4/2012 | Milne et al. |
| 2012/0133519 A1 | 5/2012 | Milne et al. |
| 2012/0136222 A1 | 5/2012 | Doyle et al. |
| 2012/0137249 A1 | 5/2012 | Milne et al. |
| 2012/0137250 A1 | 5/2012 | Milne et al. |
| 2012/0167885 A1 | 7/2012 | Masic et al. |
| 2012/0185792 A1 | 7/2012 | Kimm et al. |
| 2012/0197578 A1 | 8/2012 | Vig et al. |
| 2012/0197580 A1 | 8/2012 | Vij et al. |
| 2012/0211008 A1 | 8/2012 | Perine et al. |
| 2012/0216809 A1 | 8/2012 | Milne et al. |
| 2012/0216810 A1 | 8/2012 | Jafari et al. |
| 2012/0216811 A1 | 8/2012 | Kimm et al. |
| 2012/0226444 A1 | 9/2012 | Milne et al. |
| 2012/0247471 A1 | 10/2012 | Masic et al. |
| 2012/0272960 A1 | 11/2012 | Milne |
| 2012/0272961 A1 | 11/2012 | Masic et al. |
| 2012/0272962 A1 | 11/2012 | Doyle et al. |
| 2012/0277616 A1 | 11/2012 | Sanborn et al. |
| 2012/0279501 A1 | 11/2012 | Wallace et al. |
| 2012/0304995 A1 | 12/2012 | Kauc |
| 2012/0304997 A1 | 12/2012 | Jafari et al. |
| 2013/0000644 A1 | 1/2013 | Thiessen |
| 2013/0006133 A1 | 1/2013 | Doyle et al. |
| 2013/0006134 A1 | 1/2013 | Doyle et al. |
| 2013/0008443 A1 | 1/2013 | Thiessen |
| 2013/0025596 A1 | 1/2013 | Jafari et al. |
| 2013/0025597 A1 | 1/2013 | Doyle et al. |
| 2013/0032151 A1 | 2/2013 | Adahan |
| 2013/0047989 A1 | 2/2013 | Vandine et al. |
| 2013/0053717 A1 | 2/2013 | Vandine et al. |
| 2013/0074844 A1 | 3/2013 | Kimm et al. |
| 2013/0081536 A1 | 4/2013 | Crawford, Jr. et al. |
| 2013/0104896 A1 | 5/2013 | Kimm et al. |
| 2013/0146055 A1 | 6/2013 | Jafari et al. |
| 2013/0167842 A1 | 7/2013 | Jafari et al. |
| 2013/0167843 A1 | 7/2013 | Kimm et al. |
| 2013/0192599 A1 | 8/2013 | Nakai et al. |
| 2013/0220324 A1 | 8/2013 | Jafari et al. |
| 2013/0255682 A1 | 10/2013 | Jafari et al. |
| 2013/0255685 A1 | 10/2013 | Jafari et al. |
| 2013/0284172 A1 | 10/2013 | Doyle et al. |
| 2013/0284177 A1 | 10/2013 | Li et al. |
| 2014/0000606 A1 | 1/2014 | Doyle et al. |
| 2014/0012150 A1 | 1/2014 | Milne et al. |
| 2014/0034054 A1 | 2/2014 | Angelico et al. |

FOREIGN PATENT DOCUMENTS

| | | |
|---|---|---|
| CN | 1960671 | 5/2007 |
| CN | 100544670 C | 9/2009 |

(56) References Cited

FOREIGN PATENT DOCUMENTS

| | | |
|---|---|---|
| DE | 69121781 | 12/1991 |
| DE | 10213905 | 10/2002 |
| EP | 0459647 | 12/1991 |
| EP | 982043 | 3/2000 |
| EP | 1491227 | 12/2004 |
| EP | 858352 | 1/2005 |
| EP | 1715787 | 11/2006 |
| EP | 1972356 | 9/2008 |
| EP | 1515767 | 8/2009 |
| ES | 2094198 | 12/1991 |
| JP | 04231067 | 8/1992 |
| JP | 3183527 | 7/2001 |
| WO | WO 9014852 | 12/1990 |
| WO | WO 9214505 | 9/1992 |
| WO | WO 9308857 | 5/1993 |
| WO | WO 9715343 | 5/1997 |
| WO | WO 9812965 | 4/1998 |
| WO | WO 9951292 | 10/1999 |
| WO | WO 9962580 | 12/1999 |
| WO | WO 00/10634 | 3/2000 |
| WO | WO 0078380 | 12/2000 |
| WO | WO 01/00264 | 1/2001 |
| WO | WO 01/00265 | 1/2001 |
| WO | WO 0174430 | 10/2001 |
| WO | WO 0228460 | 4/2002 |
| WO | WO 0232488 | 4/2002 |
| WO | WO 03008027 | 1/2003 |
| WO | WO 04000114 | 12/2003 |
| WO | WO 2004047621 | 6/2004 |
| WO | WO 2005004780 | 1/2005 |
| WO | WO 2005077268 | 8/2005 |
| WO | WO 2007102866 | 9/2007 |
| WO | WO 2007145948 | 12/2007 |

OTHER PUBLICATIONS

7200 Ventilatory System: Addendum/Errata. Nellcor Puritan Bennett, Part No. 4-023576-00, Rev. A, Apr. 1998, pp. 1-32.
800 Operator's and Technical Reference Manual. Series Ventilator System, Nellcor Puritan Bennett, Part No. 4-070088-00, Rev. L, Aug. 2010, pp. 1-476.
840 Operator's and Technical Reference Manual. Ventilator System, Nellcor Puritan Bennett, Part No. 4-075609-00, Rev. G, Oct. 2006, pp. 1-424.
Castro, A.A.M. et al., "Respiratory Muscle Assessment in Predicting Extubation Outcome in Patients With Stroke", Arch Bronconeumol. 2012. doi:10.1016/j.arbres.2012.02.017, 6 pgs.
Gayan-Ramirez, Ghislaine et al., "Intermittent Spontaneous breathing protects the rat diaphragm form mechanical ventilation effects", Crit. Care Med., 2005, vol. 33, No. 12, pp. 2804-2809.
Hamid, Q. et al., "Physiologic Basis of Respiratory Disease", 2005, ATS/ERS Statement on Respiratory Muscle Testing, American Journal of Respiratory and Critical Care Medicine, vol. 166, 2002, 22 pgs.
Hudson, Matthew B. et al., "Both high level pressure support ventilation and controlled mechanical ventilation induce diaphragm dysfuntion and atrophy", Crit. Care Med., 2012, vol. 40, No. 4, pp. 1254.1260.
Mador, M. et al., "Effect of Inspiratory Muscle Fatigue on Inspiratory Muscle Relaxation Rates in Healthy Subjects", Chest, 1992; 102, pp. 1767-1773.
Nunez, Belen et al., "Recording of Possible Diaphragm Fatigue under Neurally Adjusted Ventilatory Assist", Am. J. Respiratory Crit. Care Med., 2011; 184: pp. 1213-1214.
Pourriat, J. L., M.D. et al., "Diaphragmatic Fatigue and Breathing Pattern during Weaning from Mechanical Ventilation in COPD Patients", Chest, 90: 5, Nov. 1986, pp. 703-707.

* cited by examiner

SYSTEMS AND METHODS FOR MONITORING, MANAGING, AND/OR PREVENTING FATIGUE DURING VENTILATION

INTRODUCTION

Medical ventilator systems have long been used to provide ventilatory and supplemental oxygen support to patients. These ventilators typically comprise a source of pressurized oxygen which is fluidly connected to the patient through a conduit or tubing. As each patient may require a different ventilation strategy, modern ventilators can be customized for the particular needs of an individual patient. For example, several different ventilator modes have been created to provide better ventilation for patients in various different scenarios.

MONITORING, MANAGING, AND PREVENTING FATIGUE DURING VENTILATION

This disclosure describes systems and methods for determining patient fatigue during ventilation of a patient. The disclosure describes novel notification and/or management of patient fatigue during ventilation. Further, the disclosure describes system and methods for preventing diaphragm fatigue or weakness.

In part, this disclosure describes a method for ventilating a patient with a ventilator. The method includes:
 a) monitoring a plurality of fatigue indicators;
 b) establishing a baseline for the fatigue indicators;
 c) determining a change from the baseline based on the monitored fatigue indicators;
 d) comparing the change to a corresponding fatigue threshold;
 e) detecting respiratory fatigue based on the step of comparing the change to the fatigue threshold; and
 f) displaying a fatigue notification after the step of detecting respiratory fatigue.

Yet another aspect of this disclosure describes a ventilator system that includes: a pressure generating system, a ventilation tubing system, a plurality of sensors, a baseline module, a fatigue module, a notification module, and a graphical user interface. The pressure generating system is adapted to generate a flow of breathing gas. The ventilation tubing system includes a patient interface for connecting the pressure generating system to a patient. The plurality of sensors is operatively coupled to at least one of the pressure generating system, the patient, and the ventilation tubing system. The plurality of sensors monitors a plurality of parameters to generate sensor output. The baseline module determines a baseline for a plurality of fatigue indicators. The baseline module further determines a change in the fatigue indicators from the baseline based on the sensor output. The fatigue module compares the change to corresponding fatigue thresholds. The fatigue module further determines that the patient is fatigued based on the comparisons. Based on this comparison, the fatigue module determines that the patient is fatigued. The notification module determines an appropriate notification. The graphical user interface displays the appropriate notification received from the notification module. The appropriate notification message notifies a clinician that the fatigue module determined that the patient is fatigued The disclosure further describes a computer-readable medium having computer-executable instructions for performing a method for ventilating a patient with a ventilator. The method includes:
 a) repeatedly monitoring a plurality of fatigue indicators;
 b) repeatedly establishing a baseline for the fatigue indicators;
 c) repeatedly determining a change from the baseline based on the monitored fatigue indicators;
 d) repeatedly comparing the change to a fatigue threshold;
 e) detecting respiratory fatigue based on the step of comparing the change to the fatigue threshold; and
 f) displaying a fatigue notification after the step of detecting respiratory fatigue.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The following drawing figures, which form a part of this application, are illustrative of embodiments of systems and methods described below and are not meant to limit the scope of the invention in any manner, which scope shall be based on the claims appended hereto.

DETAILED DESCRIPTION

Figure 1:
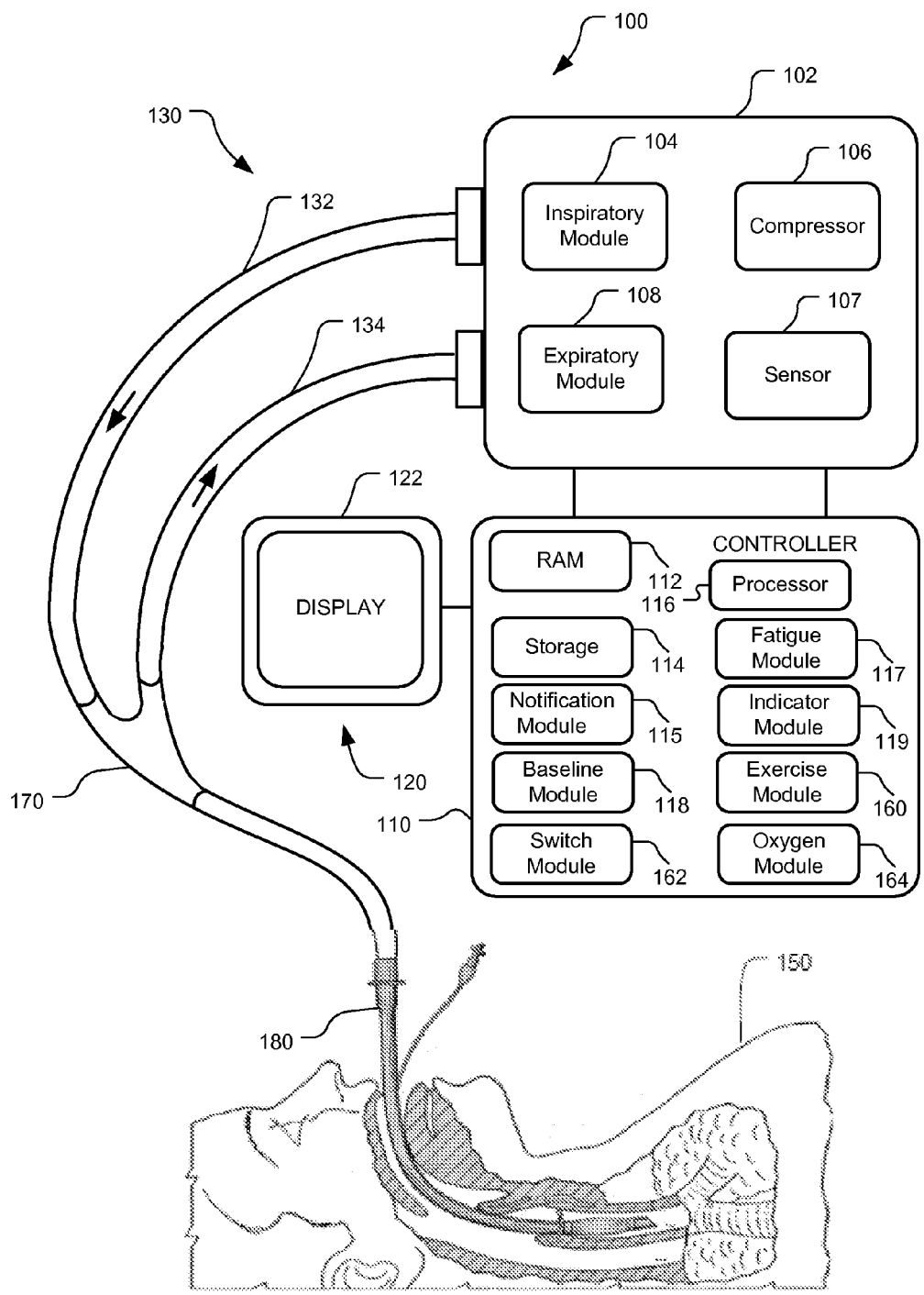
FIG. 1 illustrates an embodiment of a ventilator.

Although the techniques introduced above and discussed in detail below may be implemented for a variety of medical devices, the present disclosure will discuss the implementation of these techniques in the context of a medical ventilator for use in providing ventilation support to a human patient. A person of skill in the art will understand that the technology described in the context of a medical ventilator for human patients could be adapted for use with other systems such as ventilators for non-human patients and general gas transport systems.

Medical ventilators are used to provide a breathing gas to a patient who may otherwise be unable to breathe sufficiently. In modern medical facilities, pressurized air and oxygen sources are often available from wall outlets. Accordingly, ventilators may provide pressure regulating valves (or regulators) connected to centralized sources of pressurized air and pressurized oxygen. The regulating valves function to regulate flow so that respiratory gas having a desired concentration of oxygen is supplied to the patient at desired pressures and rates. Ventilators capable of operating independently of external sources of pressurized air are also available.

While operating a ventilator, it is desirable to control the percentage of oxygen in the gas supplied by the ventilator to the patient. Further, as each patient may require a different ventilation strategy, modern ventilators can be customized for the particular needs of an individual patient. For example, several different ventilator breath types have been created to provide better ventilation for patients in various different scenarios.

For example, with the objective providing mechanical ventilator that is more synchronous with a patient, some breath types incorporate positive feedback algorithms. With positive feedback algorithms, the amount of support provided by the ventilator is proportional to the monitored patient's work of breathing. Examples of breath types that utilized positive feedback algorithms are proportional assist (PA), tube compensation (TC), and a diaphragmatic electromyography adjusted (DEA) breath type. These breath types provide support in proportion to monitored work of breathing.

In mechanical ventilation, a proportional assist (PA) breath type refers to a type of ventilation in which the ventilator acts as an inspiratory amplifier that provides pressure support based on the patient's work of breathing. The degree of amplification (the "support setting") is set by an operator, for example as a percentage based on the patient's work of breathing (WOB). As used herein, the term "work of breathing" is intended to include any method for determining the amount effort the patient utilizes to breathe, including work of breathing (Joules/Liter), power of breathing (Joules/minute), oxygen cost of breathing ($VO_2$), pressure time product, and tension time index. In one implementation of a PA breath type, the ventilator may continuously monitor the patient's instantaneous inspiratory flow and instantaneous net lung volume, which are indicators of the patient's inspiratory WOB. These signals, together with ongoing estimates of the patient's lung compliance and lung resistance, allow the ventilator to compute a WOB and derive therefrom a target pressure to provide the support that assists the patient's inspiratory muscles to the degree selected by the operator as the support setting.

Various methods are known for calculating work of breathing and any suitable method may be used. For example, methods exist that calculate work of breathing from sensors attached to the body to detect neural or muscular activity as well as methods that determine a work of breathing based on respiratory flow, respiratory pressure or a combination of both flow and pressure.

In a PA breath type, the patient's work of breathing, the elastic work of breathing component, and/or the resistive WOB component may be estimated by inputting measurements from various sensors into the breathing algorithms. Typically, none of the instantaneous inspiratory pressure, the instantaneous flow, or the resulting volume are set by the clinician. Because the PA breath type harmoniously links the ventilator to the patient, the patient effectively "drives" the ventilator. By appropriately setting the value of the proportionality (% support or support setting) control, the clinician may effectively partition the total work of breathing between the patient and the ventilator.

The DEA breath type delivers inspiration and expiration during ventilation of a spontaneously breathing patient based on monitored neural respiratory output. Similar to the PA breath type, the DEA breath type utilizes the patient's own respiratory demand or work of breathing to determine the level of assistance to provide the patient. The neural respiratory output, which the act of breathing depends on, is the result of a rhythmic discharge from the center of brain. The discharge is carried to the diaphragm muscles cells via the phrenic nerve causing the diaphragm muscles to contract. The contraction of diaphragm muscles causes the lungs to expand dropping pressure in the airways of the lungs to provide an inflow of air into the lungs.

The neural output is the captured electrical activity of the diaphragm (Edi). The Edi is then fed to the ventilator and used by the ventilator to assist the patient's breathing. Because the ventilator and the diaphragm are triggered utilizing the same signal, the mechanical coupling between the ventilator and the diaphragm is almost instantaneous.

However, if a patient becomes fatigued, the patient work of breathing may sharply decrease. In positive feedback breath types, support is withdrawn as the patient decreases his or her work of breathing. Therefore, the patient receives less support as the patient become more fatigued, which may cause the patient's fatigue to worsen.

Current ventilators do not monitor, measure and/or estimate the fatigue of a patient. Patient fatigue could result in longer ventilation times and worsening of the patient's condition. Accordingly, the systems and methods disclosed herein detect patient fatigue. In further embodiments, the systems and method disclosed herein display a fatigue notification based on a detected patient fatigue. In additional embodiments, the systems and methods disclosed herein automatically change parameters based on a detected patient fatigue. The term "parameter(s)" as used herein refers to any variable(s) that can be input into the ventilator, monitored by the ventilator, determined by the ventilator, implemented by the ventilator, and/or selected by the ventilator. In some embodiments, after an automatic change in parameters, the systems and methods disclosed herein may check to confirm mitigation of the detected fatigue.

Further, patients that are ventilated for an extended period of time in a mandatory mode of ventilation may develop diaphragmatic weakness. The non-use of the diaphragm for the extended period of time may lead to diaphragm atrophy causing the diaphragmatic weakness or a predilection for developing fatigue. A mandatory mode delivers mandatory breaths to a patient based on a set respiratory rate. During a mandatory mode of ventilation, the patent cannot influence when inspiration or exhalation occurs. Accordingly, the systems and methods disclosed herein provide the diaphragm with exercise intermittently during the mandatory mode of ventilation. The diaphragm is provided with exercise by switching from the mandatory mode of ventilation to a spontaneous mode of ventilation after a set time period. During a spontaneous mode of ventilation, inspiration and/or exhalation is delivered upon the detection of inspiratory and/or expiratory effort by the patient based on a trigger type. However, for safety measures, inspiration and exhalation may be delivered after a predetermined amount of time passes to insure that the patient receives breathing gas in the event the patient stops making or the patient does not make any inspiratory and/or expiratory patient efforts. This exercise period expires after a predetermined exercise time and/or if no inspiratory triggers are detected by the spontaneous mode of ventilation during the excise period. Further, the exercise period expires if patient fatigue is detected. Additionally, the exercise period expires if a trend towards patient fatigue is detected. When the exercise period expires, the ventilator is switched back to the previously utilized mandatory mode of ventilation.

In some embodiments, a patient's diaphragm may develop weakness during an assist/control mode, because the ventilator may still be performing the bulk of the work for the patient during ventilation. Accordingly, the systems and methods disclosed herein may also provide the diaphragm with exercise intermittently during the assist/control mode of ventilation. The diaphragm is provided with exercise by switching from the assist/control mode of ventilation to a spontaneous mode of ventilation after a set time period.

FIG. 1 is a diagram illustrating an embodiment of an exemplary ventilator 100 connected to a human patient 150. Ventilator 100 includes a pneumatic system 102 (also referred to as a pressure generating system 102) for circulating breathing gases to and from patient 150 via the ventilation tubing system 130, which couples the patient 150 to the pneumatic system 102 via an invasive (e.g., endotracheal tube, as shown) or a non-invasive (e.g., nasal mask) patient interface 180.

Ventilation tubing system 130 (or patient circuit 130) may be a two-limb (shown) or a one-limb circuit for carrying gases to and from the patient 150. In a two-limb embodiment, a fitting, typically referred to as a "wye-fitting" 170, may be provided to couple a patient interface 180 (as shown, an endotracheal tube) to an inspiratory limb 132 and an expiratory limb 134 of the ventilation tubing system 130.

Pneumatic system 102 may be configured in a variety of ways. In the present example, pneumatic system 102 includes an expiratory module 108 coupled with the expiratory limb 134 and an inspiratory module 104 coupled with the inspiratory limb 132. Compressor 106 or other source(s) of pressurized gases (e.g., air, oxygen, and/or helium) is coupled with inspiratory module 104 and the expiratory module 108 to provide a gas source for ventilatory support via inspiratory limb 132.

The inspiratory module 104 is configured to deliver gases to the patient 150 according to prescribed ventilatory settings. In some embodiments, inspiratory module 104 is configured to provide ventilation according to various breath types, e.g., volume-control (VC), pressure-control (PC), volume support (VS), pressure support (PS), a volume-targeted-pressure-control (VC+), TC, DEA, PA, or via any other suitable breath types.

The expiratory module 108 is configured to release gases from the patient's lungs according to prescribed ventilatory settings. Specifically, expiratory module 108 is associated with and/or controls an expiratory valve for releasing gases from the patient 150.

The ventilator 100 may also include one or more sensors 107 communicatively coupled to ventilator 100. The sensors 107 may be located in the pneumatic system 102, ventilation tubing system 130, and/or on the patient 150. The embodiment of FIG. 1 illustrates a sensor 107 in pneumatic system 102.

Sensors 107 may communicate with various components of ventilator 100, e.g., pneumatic system 102, other sensors 107, processor 116, notification module 115, fatigue module 117, baseline module 118, indicator module 119, switch module 162, exercise module 160, oxygen module 164 and/or any other suitable components and/or modules. In one embodiment, sensors 107 generate output and send this output to pneumatic system 102, other sensors 107, processor 116 notification module 115, fatigue module 117, baseline module 118, indicator module 119, switch module 162, exercise module 160, oxygen module 164 and/or any other suitable components and/or modules. Sensors 107 may employ any suitable sensory or derivative technique for monitoring one or more parameters associated with the ventilation of a patient 150. Sensors 107 may detect changes in parameters indicative of patient triggering, for example. Sensors 107 may be placed in any suitable location, e.g., within the ventilatory circuitry or other devices communicatively coupled to the ventilator 100. Further, sensors 107 may be placed in any suitable internal location, such as, within the ventilatory circuitry or within components or modules of ventilator 100. For example, sensors 107 may be coupled to the inspiratory and/or expiratory modules for detecting changes in, for example, circuit pressure and/or flow. In other examples, sensors 107 may be affixed to the ventilatory tubing or may be embedded in the tubing itself. According to some embodiments, sensors 107 may be provided at or near the lungs (or diaphragm) for detecting a pressure in the lungs. Additionally or alternatively, sensors 107 may be affixed or embedded in or near wye-fitting 170 and/or patient interface 180. Indeed, any sensory device useful for monitoring changes in measurable parameters during ventilatory treatment may be employed in accordance with embodiments described herein.

As should be appreciated, with reference to the Equation of Motion, parameters are highly interrelated and, according to embodiments, may be either directly or indirectly monitored. That is, parameters may be directly monitored by one or more sensors 107, as described above, or may be indirectly monitored or estimated by derivation according to the Equation of Motion.

The pneumatic system 102 may include a variety of other components, including mixing modules, valves, tubing, accumulators, filters, etc. Controller 110 is operatively coupled with pneumatic system 102, signal measurement and acquisition systems, and an operator interface 120 that may enable an operator to interact with the ventilator 100 (e.g., change ventilator settings, select operational modes, view monitored parameters, etc.).

In one embodiment, the operator interface 120 of the ventilator 100 includes a display 122 communicatively coupled to ventilator 100. Display 122 provides various input screens, for receiving clinician input, and various display screens, for presenting useful information to the clinician. In one embodiment, the display 122 is configured to include a graphical user interface (GUI). The GUI may be an interactive display, e.g., a touch-sensitive screen or otherwise, and may provide various windows and elements for receiving input and interface command operations. Alternatively, other suitable means of communication with the ventilator 100 may be provided, for instance by a wheel, keyboard, mouse, or other suitable interactive device. Thus, operator interface 120 may accept commands and input through display 122. Display 122 may also provide useful information in the form of various ventilatory data regarding the physical condition of a patient 150. The useful information may be derived by the ventilator 100, based on data collected by a processor 116, and the useful information may be displayed to the clinician in the form of graphs, wave representations, pie graphs, text, or other suitable forms of graphic display. For example, patient data may be displayed on the GUI and/or display 122. Additionally or alternatively, patient data may be communicated to a remote monitoring system coupled via any suitable means to the ventilator 100.

Controller 110 may include memory 112, one or more processors 116, storage 114, and/or other components of the type commonly found in command and control computing devices. Controller 110 may further include a notification module 115, fatigue module 117, baseline module 118, indicator module 119, switch module 162, exercise module 160, and/or oxygen module 164 configured to deliver gases to the patient 150 according to prescribed breath types as illustrated in FIG. 1. In alternative embodiments, the notification module 115, fatigue module 117, baseline module 118, indicator module 119, switch module 162, exercise module 160, and/or oxygen module 164 may be located in other components of the ventilator 100, such as the pressure generating system 102 (also known as the pneumatic system 102).

The memory 112 includes non-transitory, computer-readable storage media that stores software that is executed by the processor 116 and which controls the operation of the ventilator 100. In an embodiment, the memory 112 includes one or more solid-state storage devices such as flash memory chips. In an alternative embodiment, the memory 112 may be mass storage connected to the processor 116 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 116. That is, computer-readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

In some embodiments, the inspiratory module 104 receives a breath type from operator selection. In some embodiments, the inspiratory module 104 receives a breath type based on ventilator selection. In some embodiments, the breath type is a positive feedback breath type, such as a DEA breath type, TC breath type, or a PA breath type. With positive feedback breath types, the amount of support provided by the ventilator is proportional to the monitored patient's work of breathing. However, if a patient becomes fatigued, the patient may decrease their work of breathing. In positive feedback breath types, support is withdrawn as the patient decreases his or her work of breathing. Therefore, the patient receives less support as the patient become more fatigued, which may cause the patient's fatigue to worsen. Accordingly, a basal level of pressure support may be set. The basal level of pressure support is a set pressure, pressure level, or support setting that provides the minimum amount of pressure support that the positive feedback breath type delivers regardless of the patient's WOB. Accordingly, the basal level of pressure support limits the positive feedback algorithm from reducing support beyond a predetermined threshold during the breath type.

In other embodiments, the breath type is a VC, PC, PS, VS, or VC+ breath type. In some embodiments, a negative feedback breath type is utilized. A negative feedback breath type as utilized herein refers to a breath type that provides support to the patient based inversely on the amount of WOB detected. Accordingly, the larger the patient's WOB the more support the ventilator provides during a negative feedback breath type. For example, a VS breath type and a VC+ breath type are negative feedback breath types.

The baseline module 118 determines a baseline for one or more fatigue indicators. As used herein, the "baseline" designates a normal level or desired level of the fatigue indicator for the patient. The fatigue indicator is any suitable parameter for providing an indication of patient fatigue. In an alternative embodiment, the fatigue indicator is a fatigue metric. The fatigue metric is any suitable function of two or more fatigue indicators. For example, the fatigue metric may add, subtract, divide, and/or multiply two or more fatigue indicators. The fatigue metric may be any suitable mathematical relationship between two or more fatigue indicators for determining patient fatigue.

In some embodiments, at least one of the following parameters may be utilized as the fatigue indicator: WOB, partial pressure of carbon dioxide in the blood ($PaCO_2$), the volume of carbon dioxide ($VCO_2$) produced by the patient 150, electromyography (EMG) of a respiration accessory muscle, $E_{di}$, measurement of the respiratory drive as indicated by the occlusion pressure of the airway at 100 ms ($P_{0.1}$), diaphragmatic position, $P_{di}$, maximal transdiaphragmatic pressure ($P_{di,max}$), maximal inspiration pressure ($P_{mus}$), cardiac output, velocity of muscle shortening, $V_t$, diaphragm movement, esophageal pressure ($P_{esoph}$), $P_{di}$ Maximum Relaxation Rate, estimated inspiratory muscle pressure ($P_{mus}$) Maximum Relaxation Rate, abdominal and/or rib cage muscle contractions, paradoxical breathing, exhaled alveolar volume ($V_{e\ alv}$), respiration rate, bispectral index level of sedation (BIS LOS), RSBI, tidal volume divided by inspiration time ($V_t/T_i$), diaphragm pressure divided by maximal diaphragm pressure ($P_{di}/P_{di\ max}$), inspiration time divided by total time of the breath cycle ($T_i/T_{tot}$), dead space ventilation volume divided by tidal volume ($V_d/V_t$), pressure time index ($P_{tid}$ or ($P_{di}/P_{di\ max})/(T_i/T_{tot})$), inspiration time divided by total time of the breath cycle divided by diaphragm pressure divided by maximal diaphragm pressure ($T_i/T_{tot}/P_{di}/P_{dimax}$), respiration muscle pressure divided EMG integral, the captured electrical activity of the phrenic nerve ($E_{phr}$), oxygen saturation level of the blood ($SpO_2$), minute volume (MV), and $P_{mus}$. This list exemplary only and is not meant to limit the disclosure.

In some embodiments, the fatigue indicator is taken directly from sensor output. In other embodiments, the fatigue indicator is derived (which includes estimated) from sensor output. In some embodiments, an indicator module 119 derives the fatigue indicator from sensor output. The indicator module 119 may be a separate component or may be a part of the baseline module 118, fatigue module 117, controller 110, and/or pneumatic system 102. For example, RSBI is respiratory rate divided by $V_t$. Accordingly, in some embodiments, the fatigue module 117 derives the RSBI by dividing the measured flow by the measured $V_t$, which are both received as sensor output.

In some embodiments, the fatigue indicator is a work of breathing (WOB), which may be derived by the indicator module 119. In this embodiment, the indicator module 119 receives sensor output from one or more sensors 107. The indicator module 119 derives (which includes estimating) the patients work of breathing from the sensor output. In some embodiments, the derived work of breathing is calculated by entering the sensor output into the Equation of Motion. In other embodiments, the WOB is derived by the indicator module 119 by inputting various measurements (also known as sensor output) from various sensors into breathing algorithms. In some embodiments, the sensor output is monitored inspiratory flow and/or net flow. In other embodiments, the indicator module 119 estimates at least one of resistance, elastance, and/or compliance from the sensor output in order to derive the WOB of the patient 150. However, the indicator module 119 may utilize any known systems or methods for calculating a WOB of the patient 150 from sensor output. For example, methods exist that calculate work of breathing from sensors 107 attached to the body to detect neural or muscular activity as well as methods that determine a work of breathing based on respiratory flow, respiratory pressure or a combination of both flow and pressure.

In some embodiments, the baseline module 118 determines a baseline for a fatigue indicator based on input from a clinician. For example, the clinician may enter the desired baseline for the patient. This allows the clinician to determine the desired baseline for a fatigue indicator. The clinician may take into account the patient's history, disease state, sex, and other factors when determining the baseline for a fatigue indicator for a patient.

In an alternative embodiment, the baseline module 118 determines a baseline for fatigue indicators by averaging sensor output for each of the fatigued indicators for a predetermined amount of time. In some embodiments, the sensors 107 monitor the parameters every computational cycle (e.g., 2 milliseconds, 5 milliseconds, 10 milliseconds, etc.). In other embodiments, the sensors 107 monitor the parameters after a predetermined number of breaths (e.g., 1 breath, 2 breaths, 3 breaths, etc.). In other embodiments, the sensors 107 monitor the parameters after a predetermined set sensor time period (e.g., 1 second, 2 seconds, 30 seconds, 1 minute, 5 minutes, etc.). Accordingly, the baseline module 118 adds the set of measurements or sensor output generated by the repeated sensor measurements for the predetermined amount of time and then divides the total by the number of measurements taken to determine the baseline. The predetermined time period may be any suitable amount of time for determining a normal or baseline parameter value for the patient 150. In some embodiments, the predetermined amount of time is 10 minutes, 30 minutes, 45 minutes, 1 hour, 1.5 hours, 2 hours, 6 hours, 12 hours, or 24 hours.

In further, embodiments, some fatigue parameters only exist in a finite number of states. Accordingly, for these fatigue indicators a predetermined state will be the baseline. These baselines may be predetermined and automatically configured on the ventilator 100. For example, absence of paradoxical breathing may be a baseline. Accordingly, the presence of paradoxical breathing is a detected change from this baseline.

In some embodiment, the predetermined amount of time starts after the ventilator 100 delivers a predetermined number of breaths (e.g., 1 breath, 2 breaths, 3 breaths, 5 breaths, etc.) from the start of ventilation. In other embodiments, the predetermined amount of time begins after a set start time, such as 1 minute after the beginning of ventilation, 5 minutes after the beginning of ventilation, 10 minutes after the beginning of ventilation, 1 hour after the beginning of ventilation, or 3 hours after the beginning of ventilation. In further embodiments, the predetermined amount of time begins after the start of a spontaneous mode of ventilation or after ventilator support has been reduced.

For example, in some implementations, the following may be utilized as baselines for the following fatigue indicators:
$PaCO_2$ is 38-42 mmHg;
$PaCO_2$ for patients with COPD 42-62 mmHg;
pH of 7.38-7.42;
$VCO_2$ of 180-200 mL/min;
$VCO_2$ of 2.5-3.5 mL/Kg/min;
$P_{0.1}$ of 1-2 $cmH_2O$;
$P_{di,max}$ is about 80 $cmH_2O$;
$P_{i,max}$ is about 80 $cmH_2O$;
$V_t$ is 5-6 mL/kg;
$P_{esoph}$ is 3-5 $cmH_2O$;
no paradoxical breathing;
respiration rate is 12-16/min for adults;
RSBI is less than 40;
$P_{di}/P_{di\ max}$ is around 5-10%;
$T_i/T_{tot}$ is about 30%; and
$V_d/V_t$ is 0.2-0.3.

After the baseline has been determined by the baseline module 118, the baseline module 118 determines a change in the fatigue indicators from the baseline based on the sensor output. A change is determined by the baseline module 118 when the current sensor output or monitor fatigue parameter is not equivalent or substantially equivalent to the baseline. In some embodiments, a fatigue parameter is considered substantially equivalent to the baseline when the difference between the fatigue parameter and the baseline is less than 1%. In other embodiments, a fatigue parameter is considered substantially equivalent to the baseline when the difference between the fatigue parameter and the baseline is less than 3%. In further embodiments, a fatigue parameter is considered substantially equivalent to the baseline when the difference between the fatigue parameter and the baseline is less than 5%.

If the baseline module 118 determines a change in the fatigue indicators from the baseline, then the baseline module 118 sends the change to the fatigue module 117. If the baseline module 118 does not determine a change in the fatigue indicators from the baseline, then the baseline module 118 continues to monitor for a change in the fatigue indicators based on the sensor output from the baseline.

The fatigue module 117 determines if a patient 150 is fatigued. The fatigue module 117 determines if a patient 150 is fatigued by comparing the change received from the baseline module 118 to a fatigue threshold. In some embodiments, the fatigue threshold is input by an operator. In other embodiments, the fatigue threshold is determined by the ventilator 100 based on known parameters, such as ideal body weight, height, weight, sex, breath type, support setting, tidal volume, etc. In some embodiments, the fatigue threshold is a detected rate of change in the fatigue indicator. This list exemplary only and is not meant to limit the disclosure.

If the detected change breaches the fatigue threshold, the fatigue module 117 of the ventilator 100 determines that the patient 150 is fatigued. If the detected change does not breach the fatigue threshold, the fatigue module 117 of the ventilator 100 determines that the patient 150 is not fatigued. In one example, the fatigue module 117 monitors a specific fatigue indicator. In an alternative example, the fatigue module 117 monitors numerous fatigue indicators to determine if any changes of the fatigue indicators breach their corresponding fatigue threshold. In another example, the fatigue module 117 monitors numerous fatigue indicators to determine if change in a predetermined number or a select group of the fatigue indicators breach their corresponding fatigue thresholds. For example, the fatigue module 117 of ventilator 100 may monitor a specific fatigue indicator, such as Rapid Shallow Breathing Index (RSBI), or may monitor numerous fatigue indicators (such as RSBI, electrical activity of the diaphragm ($E_{di}$), tidal volume ($V_t$), work of breathing (WOB), and transdiaphragmatic pressure ($P_{di}$)) to determine if any, a predetermined number, or a select group of fatigue indicators breach their corresponding fatigue thresholds.

The fatigue threshold is any suitable fatigue indicator threshold for providing an indication of patient fatigue. In embodiments, the fatigue indicator threshold is a threshold for a fatigue metric. In some embodiments, as discussed above, the fatigue indicator threshold is a detected rate of change in a fatigue indicator and/or metric. In some embodiments, the fatigue threshold is at least one of the following thresholds:

work of breathing decrease below the baseline;
work of breathing increases above the baseline followed by a decrease below the baseline;
$PaCO_2$ increases from the baseline;
$VCO_2$ decreases from the baseline;
EMG of an accessory muscle indicates use of the accessory muscle;
$E_{di}$ decreases from the baseline;
$P_{0.1}$ increases and then decreases from the baseline;
diaphragmatic position becomes flattened;
$P_{di}$; decreases from the baseline;
$P_{di,max}$ decreases from the baseline;
$P_{i,max}$ decreases from the baseline;
cardiac output does not increase from the baseline with an increasing load,
velocity of muscle shortening decreases from the baseline;
EMG time domain decreases from the baseline;
$EMG_t$ frequency domain decreases from the baseline;
$V_t$ decreases from the baseline;
diaphragm movement imaging shows reduced movement from the baseline;
$P_{esoph}$ decreases from the baseline;
$P_{di}$ Maximum Relaxation Rate decreases from the baseline;
$P_{mus}$ Maximum Relaxation Rate decreases from the baseline;
alternating abdominal/rib cage muscle contractions occur or increase in frequency from the baseline;
$V_{e\ alv}$ decreases from the baseline;
respiration rate increases followed by a decrease from the baseline;
BIS LOS is normal;
RSBI increases from the baseline;
$V_t/T_i$ decreases from the baseline;
$P_{di}/P_{di\ max}$ increases from the baseline;
$T_i/T_{tot}$ increases from the baseline;
$V_d/V_t$ increases from the baseline;
$P_{tid}$ increases from the baseline;
$T_i/T_{tot}/P_{di}/P_{dimax}$ increases from the baseline;
Respiration muscle pressure/EMG integral decreases from the baseline;
$E_{di}$ increases while $E_{phr}$ increases and $P_{di}$ decreases from the baseline;
$P_{di,max}$ decreases from the baseline;
$P_{i,max}$ decreases from the baseline;
$E_{di}$ increases and at least one of a decrease in $V_t$, a decrease in $VCO_2$, a decrease in $SpO_2$, an increase in $P_{0.1}$, and a decrease in MV from the baseline occurs;
$P_{mus}$ decreases and at least one of a decrease in $V_t$, a decrease in $VCO_2$, a decrease in $SpO_2$, and a decrease in MV from the baseline occurs;
$PaCO_2$ increases from the baseline by at least 10 mmHg,
$VCO_2$ decrease from the baseline by more than 20%,
$E_{di}$ decreases from the baseline by at least 25%,
$E_{di}$ stays the same while the velocity of muscle shortening decreases from the baseline;
$P_{0.1}$ increases above 4 cm of $H_2O$ and then decreases by at least 2 cm of $H_2O$,
$P_{di}$ decreases by at least 10% from the baseline;
$P_{di,max}$ decreases by at least 20% from the baseline;
$P_{i,max}$ decreases by at least 20% from the baseline;
velocity of muscle shortening decreases by at least 25% from the baseline;
EMG time domain is less than 50 uV;
$EMG_t$ frequency domain decreases by more than 20% from the baseline;
$V_t$ is below 4 mL/kg;
$P_{esoph}$ decreases by at least 10% from the baseline;
$P_{di}$ Maximum Relaxation Rate decreases by at least 20% from the baseline;
$P_{mus}$ Maximum Relaxation Rate decreases by at least 20% from the baseline;
presence of paradoxical breathing;
$V_{e\ alv}$ decreases by at least 20% from the baseline;
respiration rate increases above 35 breaths a minute;
respiration rate increases by at least 25% from the baseline followed by a decrease;
RSBI increases above 105;
$V_t/T_i$ decreases by 30% from the baseline;
$Pa_{di}/Pa_{di\ max}$ is above 40% from the baseline;
$T_i/T_{tot}$ is greater than 40% from the baseline;
$V_d/V_t$ increases by 20% from the baseline;
$V_d/V_t$ is greater than 40% from the baseline;
$P_{tid}$ increases above 0.15; and
$T_i/T_{tot}/P_{di}/P_{dimax}$ is greater than 40% from the baseline.

This list exemplary only and is not meant to limit the disclosure. Any suitable thresholds for determining fatigue in a patient during ventilation may be utilized by the ventilator.

In additional embodiments, the fatigue module 117 may determine the level of fatigue detected. To determine the level of fatigue detected, the fatigue module 117 may weigh how much a fatigue threshold was breached, how many fatigue thresholds were breached, and/or a rate at which any breach is increasing. The ventilator 100 may utilize a mathematical algorithm for weighing the above parameters to determine the level of fatigue detected. In some embodiments, the fatigue module 117 may list the patient fatigue as high, medium, or low. In other embodiments, a fatigue index is determined by the fatigue module 117. The fatigue index may indicate the level of fatigue experience by the patient. For example, the fatigue index may be a scale of 1-10 or 1-3. The higher the degree of patient fatigue, the higher the fatigue index determined by the ventilator (1 may be the high end or 10 and 3 may be the high end of the scale depending upon the desired index). Accordingly, in one embodiment where the fatigue module 117 detects a high level of fatigue, a fatigue index of 8 may be determined. In another embodiment, where the fatigue module 117 detects a medium level of fatigue, a fatigue index of 5 or 2 may be determined. The listed fatigue indexes above are not meant to be limiting. Any suitable indication of a patient's fatigue level may be utilized by the fatigue module 117 as the fatigue index, including symbols, colors (i.e., red, yellow, and green to designate different fatigue levels), text, numbers, and/or animations.

In some embodiments, if patient fatigue is detected by the fatigue module 117, the fatigue module 117 communicates with the notification module 115. The notification module 115 determines an appropriate notification based on the information received from the fatigue module 117. When patient fatigue is implicated, many clinicians may not be aware of adjustments to parameters that may reduce or eliminate fatigue. As such, upon detection of patient fatigue, the notification module 115 may be configured to notify the clinician that patient fatigue is implicated and/or to provide recommendations to the clinician for mitigating patient fatigue. Accordingly, the notification message may include a recommendation for mitigating patient fatigue. For example, notification module 115 may be configured to notify the clinician by displaying a notification on display 122 and/or within a window of the GUI. According to additional embodiments, the notification is communicated to and/or displayed on a remote monitoring system communicatively coupled to ventilator 100. According to alternative embodiments, the notification is any audio and/or visual notification. Alternatively, in an automated embodiment, the notification module 115 communicates with a ventilator control system, such as the controller 110 so that the recommendation may be automatically implemented to mitigate the patient fatigue.

In order to accomplish the various aspects of the notification message display, the notification module 115 may communicate with various other components and/or modules. For instance, notification module 115 may be in communication with processor 116, fatigue module 117, baseline module 118, indicator module 119, or any other suitable module or component of the ventilator 100. That is, notification module 115 may receive an indication that fatigue has been implicated by any suitable means. In addition, notification module 115 may receive information regarding one or more parameters that implicated the presence of patient fatigue and information regarding the patient's ventilator settings and treatment. Further, according to some embodiments, the notification module 115 may have access to a patient's diagnostic information (e.g., regarding whether the patient has ARDS, COPD, asthma, emphysema, or any other disease, disorder, or condition).

In some embodiments, notifications may be provided according to a hierarchical structure such that a notification may be initially presented in summarized form and, upon clinician selection, an additional detailed notification may be displayed. According to alternative embodiments, a notification is initially presented without a recommendation and, upon clinician selection, a recommendation message is displayed. Alternatively or additionally, the notification simultaneously displays a detection of patient fatigue with a recommendation message in any suitable format or configuration.

Specifically, according to some embodiments, the notification alerts the clinician as to the detection of a patient condition, a change in patient condition, or an effectiveness of ventilator treatment. For example, the notification message determined by the notification module 115 may alert the clinician that fatigue has been detected and the parameters that indicated the patient fatigue (i.e., WOB, RSBI, $V_t$, $E_{di}$, and etc.). The notification may further alert the clinician regarding the particular breach or level of breach of the particulars parameter(s) that implicated patient fatigue (e.g., WOB, cardiac output, $P_{di}$, $VCO_2$, etc.) For example, the notification may recite that patient fatigue is detected and then list the fatigue indicator that indicated the patient fatigue.

In some embodiments, the notification recites the following messages:
    fatigue detected;
    fatigue warning;
    fatigue implicated; and
    fatigue notification.
In some embodiments, the notification may further recite the one or more fatigue indicator measurements that indicated the patient fatigue. In other embodiments, the notification may also recite the one or more fatigue thresholds. In other embodiments, the level of fatigue is displayed in the notification. For example, the notification may list a high, medium, or low level of patient fatigue is detected. In other embodiments, a fatigue index may be listed in the notification. As discussed above the fatigue index may indicate the level of patent fatigue detected by the fatigue module 117. Further, any suitable indication of a patient's fatigue level may be displayed by the notification module 115 as the fatigue index, including symbols, colors (i.e., red, yellow, and green to designate different fatigue levels), text, numbers, and/or animations.

Additionally, according to embodiments as discussed above, the notification may provide various suggestions to the clinician for addressing detected patient fatigue. In some embodiments, the recommendation includes any change in ventilation that provides the patient with additional ventilation support. According to additional embodiments, the notification may be based on the particular parameter(s) that implicated the patient fatigue. Additionally or alternatively, the recommendation may be based on current ventilator settings (e.g., breath type). Additionally or alternatively, the recommendation may be based on a diagnosis and/or other patient attributes. Further still, the recommendation may include a primary recommendation message and a secondary recommendation message. For example, the primary recommendation message may recite, "consider switching breath types" and the secondary recommendation message may recite, "consider switching to a VC+ breath type." In another example, the primary recommendation message may recite, "consider utilizing a basal level of pressure support in the PA breath" and the secondary recommendation may recite, "consider utilizing 5 cm $H_2O$ as your basal level of support." In an additional example, the primary recommendation message may recite, "consider switching to invasive ventilation" and the secondary recommendation may recite, "consider switching to a negative feedback breath type."

As discussed above, the basal level of pressure support limits the positive feedback during a positive feedback breath type from reducing support beyond a predetermined threshold. Therefore, the patient receives at least this minimal amount of pressure support when a basal level of pressure support is utilized. Accordingly, the basal level of pressure support may mitigate detected patient fatigue. The basal level of pressure support may vary based on the patient. In some embodiments, the basal level of pressure support is at least 5 cm $H_2O$. In other embodiments, the basal level of pressure support is at least 8 cm $H_2O$.

Notification module 115 may be responsible for generating a notification via any suitable method or system. For example, the notification may be provided as a tab, banner, dialog box, or other similar type of display. Further, the notification may be provided along a border of the graphical user interface, near an alarm display or bar, or in any other suitable location. A shape and size of the notification may further be optimized for easy viewing with minimal interference to other ventilator displays. The notification message may be further configured with a combination of icons and text such that the clinician may readily identify the message as a notification message.

The notification module 115 may be responsible for generating one or more recommendations via any suitable systems or methods. The one or more recommendations may provide suggestions and information regarding addressing the detected patient fatigue. In some embodiments, the one or more recommendations identifies the parameters that implicated the detected condition, provides suggestions for adjusting the one or more parameters to address the detected fatigue, provides suggestions for checking ventilator equipment or patient position, and/or provides other helpful information. For example, if fatigue is implicated, the notification may include one or more of the following recommendations:
    consider switching to invasive ventilation;
    consider switching to a negative feedback breath type;
    consider switching to a PS, PC, VC, VC+, or VS breath type;
    consider increasing ventilation support;

consider increasing a support setting in the PA breath type;

consider increasing a support setting in the DEA breath type;

consider increasing a support setting in a positive feedback breath type;

consider increasing set respiratory rate;

consider utilizing a basal level of support in the PA breath type;

consider utilizing a basal level of support in the DEA breath type; and consider utilizing a basal level of support in a positive feedback breath type.

As discussed above, in some embodiments, after patient fatigue is detected by the fatigue module 117, the notification module 115 recommends switching from non-invasive ventilation to invasive ventilation. Studies have shown that waiting too long before switching from non-invasive ventilation to invasive patient ventilation when a patient is responding poorly to ventilation (e.g., detecting patient fatigue) has been linked to an increased mortality rate.

Accordingly, if patient fatigue is detected, the notification module 115 may recommend switching from a non-invasive ventilation (i.e., use of a nasal mask and other setting changes) to invasive ventilation (i.e. use of an endotracheal tube and other setting changes). However, since the ventilators cannot automatically implement such a change, the clinician based on the patient, the patient's history, and measured parameters must determine if switching from non-invasive ventilation to an invasive ventilation is warranted.

As discussed above, in an automated embodiment, the notification module 115 communicates with a ventilator control system, such as the controller 110, so that the recommendation may be automatically implemented to mitigate the patient fatigue. The automated implementation of the recommendation may be performed automatically by the ventilator 100 or performed automatically upon user selection of an automated response mode. In some embodiments, the notification module 115 of the ventilator 100 automatically implements the recommendations. In other embodiments, any suitable ventilator component with a processor automatically implements the recommendations. For example, if patient fatigue is detected during a positive feedback breath type, the notification module 115 of ventilator 100 may automatically implement a basal level of pressure support. In an alternative embodiment, if patient fatigue is detected during a positive feedback breath type (e.g., PA), the notification module 115 of ventilator 100 automatically switches to non-positive feedback breath type. For example, the ventilator 100 may switch to a negative feedback breath type (e.g., VS or VC+) or to another breath type (e.g., VC, VS, and PC). In some embodiments, notification module 115 notifies the clinician of the automated adjustment to account for detected patient fatigue. In one embodiment, the notification module 115 of ventilator 100 displays a notification indicating that patient fatigue is detected and the automated adjustment made to account for this fatigue. For example, if patient fatigue is detected during a positive feedback breath type, the notification may recite, "fatigue detected" and "basal level of pressure support implemented to mitigate fatigue." In another example, if patient fatigue is detected during a positive feedback breath type, the notification may recite, "fatigue implicated" and "switched to a PC breath type to mitigate fatigue." This list is merely exemplary. Any of the above recommendations that are suitable for automatic implementation may be automatically implemented by the ventilator after patient fatigue is detected by the ventilator.

In some embodiments, if a recommendation is automatically implemented by the ventilator, the fatigue module 117 confirms that the detected patient fatigue was mitigated by the implemented response. In this embodiment, the fatigue module 117 after a predetermined rest time that begins when the recommendation is implemented, re-measures from the generated sensor output the one or more changes in fatigue indicators that previously breached a threshold to indicate the detected patient fatigue. In some embodiments, the predetermined rest time is several minutes to a few hours. For example, the predetermined rest time is about 30 minutes, 45 minutes, 1 hour, 1.25 hours, 1.5 hours, 1.75 hours, 2 hours, 3 hours, 4 hours, 5 hours, 6 hours, 7 hours, 8 hours, 9 hours, 10 hours, 11 hours, or 12 hours. However, any suitable amount of time to provide the patient with rest to mitigate fatigue may be utilized by the ventilator 100. The implemented recommendation provides the patient with additional ventilation support and thereby is allowing the patient to rest during the predetermined rest time. The one or more changes in fatigue indicators of the patient that breached a threshold to indicate the patient's fatigue are referred to herein as "breached parameters." The one or more changes in fatigue indicators of the patient determined after the predetermined rest time are referred to herein as "rested parameters." For example, if a determined RSBI of the patient indicated the patient fatigue, then after the predetermined rest time the RSBI of the patient would be determined. The determined RSBI after the predetermined rest time is the rested parameter. The RSBI determined before the predetermined rest time that indicated the breach is the breached parameter. In some embodiments, the ventilator settings utilized to determine the ventilation of the patient, such as breath type, are changed back to settings that were previously utilized during the detection of the patient fatigue before determining the breached parameters. The settings are returned to the settings utilized during fatigue detection to ensure that any difference between the rested parameters and the baseline cannot be attributed to the different ventilator settings utilized during ventilation of the patient at the time of measurement.

The fatigue module 117 compares the rested parameters to the baseline. The fatigue module 117 determines if the implemented recommendation mitigated the determined fatigue based on the comparison of the rested parameters to the baseline. If the fatigue module 117 determines that the rested parameters have improved by a predetermined amount when compared to the baseline, then the fatigue module 117 determines that the implemented recommendation mitigated the patient fatigue. However, if the fatigue module 117 determines that the rested parameters have not improved by a predetermined amount when compared to the baseline, then the fatigue module 117 determines that the implemented recommendation did not mitigate the patient fatigue.

In some embodiments, the rested parameter is considered to be improved if the rested parameter improved by 50% or more when compared to the baseline. In some embodiments, the rested parameter is considered to be improved if the rested parameter improved by 80% or more when compared to the baseline. In other embodiments, the rested parameter is considered to be improved if the rested parameter no longer breaches the predetermined threshold for determining patient fatigue when compared to the baseline. For example, if the rested parameters are a rested RSBI of 85 and a rested spontaneous $V_t$ is 5 mL/kg, then the fatigue module 117 determines that the patient fatigue was mitigated by the implemented recommendation because the rested parameters have improved so much that the rested parameters no longer breach the fatigue threshold when compared to the baseline.

If the implemented recommendation, which provided the patient with additional ventilator support in order to rest the patient, mitigated the fatigue of the patient, then the patient is confirmed to have been fatigued. Accordingly, in some embodiments, if the fatigue module 117 determines that the implemented recommendation did mitigate the fatigue, then the fatigue module 117 instructs the notification module 115 to display a notification relating to the mitigated fatigue.

The notification module 115 displays notifications relating to the mitigated fatigue based on the instructions from the fatigue module 117. The notification includes a notification that the fatigue was fixed by the implemented recommendation. The notification may further include a notice that the patient fatigue was the correct assessment, that the implemented recommendation was sufficient to mitigate the patient fatigue, and/or that the patient's condition is improved. In some embodiments, the notification may further include one or more recommendations for changing the level of ventilatory support for the patient now that the patient is no longer fatigued.

In further embodiments, the notification may further include a reference to the rested parameters, the breached parameters, the baseline, and/or the predetermined thresholds of the breached parameters. These notifications include any of the features discussed above for a notification message, such as a hierarchical structure, display on a remote monitoring system, and/or a summarize format with recommendations offered upon selection. For example, the notification relating to the mitigated fatigue may include:

Fatigue mitigated;
Consider switching to a positive feedback breath type;
Patient fatigue confirmed;
Fatigue reduced by at least 80%; and
etc.

If the implemented recommendation, which provided the patient with additional ventilator support in order to rest the patient, did not mitigate the fatigue, then the patient may not have been fatigued, the implemented recommendation may not have been sufficient to mitigate the patient fatigue, and/or the patient's condition may have deteriorated. Accordingly, in some embodiments, if the fatigue module 117 determines that the implemented recommendation did not mitigate the fatigue, then the fatigue module 117 instructs the notification module 115 to display a notification relating to the unmitigated fatigue.

The notification module 115 displays notification relating to the unmitigated fatigue based on the instructions from the fatigue module 117. The notification includes a notification that the fatigue was not fixed by the implemented recommendation. The notification may further include a notice that the patient fatigue was an incorrect assessment, that the implemented recommendation was insufficient to mitigate the patient fatigue, and/or that the patient's condition may have deteriorated. In some embodiments, the notification may further include one or more recommendations for dealing with the unmitigated fatigue. In further embodiments, the notification may further include a reference to the rested parameters, the breached parameters, and/or the predetermined thresholds of the breached parameters. These notifications include any of the features discussed above for a notification message, such as a hierarchical structure, display on a remote monitoring system, and/or a summarize format with recommendations offered upon selection. For example, the notification relating to the unmitigated fatigue may include:

Fatigue treatment failed;
Patient condition deteriorating-Fatigue unmitigated;
Warning patient not responding to fatigue treatment;
Warning patient not fatigued, consider checking other causes of the change in the fatigue indicator;
Warning fatigue detected in error, consider checking other parameters to determine the cause of the patient's detected negative condition; and
etc.

In some embodiments, the ventilator 100 includes an exercise module 160 and a switch module 162. In these embodiments, the ventilator 100 may further include an oxygen module 164. As discussed above, patients that are ventilated for an extended period of time in a mandatory mode of ventilation may develop diaphragmatic weakness. The non-use of the diaphragm for the extended period of time during the mandatory mode may lead to diaphragm atrophy causing the diaphragmatic weakness or fatigue. Accordingly, the exercise module 160 and the switch module 162 allow the ventilator 100 to exercise the diaphragm of the patient 150 in an attempt to mitigate or prevent the diaphragm atrophy and/or weakness.

In some embodiments, the switch module 162 switches from a set mandatory mode of ventilation to a spontaneous mode of ventilation after a predetermined amount of time expires or after a specific event, such as a predetermined number of breaths, inspirations, or cycle. In some embodiments, the switch module 162 is activated upon clinician input. In other embodiments, the switch module 162 is activated after a patient has been ventilated based on a mandatory mode of ventilation for a certain amount of time or after a predetermined number of breaths. The certain amount of mandatory mode time may be input by the clinician or predetermined by the ventilator. In some embodiments, a patient's diaphragm may develop weakness during an assist/control mode, because the ventilator may still be performing the bulk of the work for the patient during ventilation. Accordingly, in this embodiment the switch module 162 switches from a set assist/control mode of ventilation to a spontaneous mode of ventilation after a predetermined amount of time expires or after a specific event, such as a predetermined number of breaths, inspirations, or cycle. If the switch module 162 is not activated, the switch module 162 does not switch from the set mandatory mode of ventilation to a spontaneous mode of ventilation when a time period expires or a set event occurs.

The predetermined amount of mandatory mode time begins with the start of the mandatory mode during ventilation. The start of the mandatory mode of ventilation is any time the ventilator is switched into a mandatory mode of ventilation from a different mode or at the beginning of ventilation just after the ventilator is turned on. In some embodiments, the predetermined amount of mandatory mode time (also referred to as a standard time period) is about 30 minutes, 45 minutes, 60 minutes, 75 minutes, 90 minutes, 105 minutes, or 120 minutes.

The mandatory mode time may be any suitable amount of time that provides an intermittent spontaneous mode often enough to prevent or mitigate diaphragm atrophy or weakness.

Several different breath types may be utilized during the mandatory mode of ventilation. In some embodiments, a pressure control (PC) breath type is utilized during the mandatory mode of ventilation. In other embodiments, a volume control (VC) breath type is utilized during the mandatory mode of ventilation. In further embodiments, a volume-controlled-pressure-targeted (VC+) breath type is utilized during the mandatory mode of ventilation.

The VC breath type allows a clinician to set a respiratory rate and to select a volume to be administered to a patient during a mandatory breath. When using VC, a clinician sets a desired tidal volume, flow wave form shape, and an inspiratory flow rate or inspiratory time. These variables determine how much volume of gas is delivered to the patient and the duration of inspiration during each mandatory breath inspiratory phase. The mandatory breaths are administered according to the set respiratory rate.

For VC, when the delivered volume is equal to the prescribed tidal volume, the ventilator may initiate exhalation. Exhalation lasts from the time at which prescribed volume is reached until the start of the next ventilator mandated inspiration. This exhalation time is determined by the respiratory rate set by the clinician and any participation above the set rate by the patient. Upon the end of exhalation, another VC mandatory breath is given to the patient.

During VC, delivered volume and flow waveforms may remain constant and may not be affected by variations in lung or airway characteristics. Alternatively, pressure readings may fluctuate based on lung or airway characteristics. According to some embodiments, the ventilator may control the inspiratory flow and then derive volume based on the inspiratory flow and elapsed time.

The PC breath type allows a clinician to select a pressure to be administered to a patient during a mandatory breath. When using the PC breath type, a clinician sets a desired pressure, inspiratory time, and respiratory rate for a patient. These variables determine the pressure of the gas delivered to the patient during each mandatory breath inspiration. The mandatory breaths are administered according to the set respiratory rate.

For the PC breath type, when the inspiratory time is equal to the prescribed inspiratory time, the ventilator may initiate exhalation. Exhalation lasts from the end of inspiration until the next inspiration. Upon the end of exhalation, another PC mandatory breath is given to the patient.

During PC breaths, the ventilator may maintain the same pressure waveform at the mouth, regardless of variations in lung or airway characteristics, e.g., respiratory compliance and/or respiratory resistance. However, the volume and flow waveforms may fluctuate based on lung and airway characteristics.

The VC+ breath type is a combination of volume and pressure control breath types that may be delivered to a patient as a mandatory breath. In particular, VC+ may provide the benefits associated with setting a target tidal volume, while also allowing for variable flow.

As may be appreciated, when resistance increases and/or compliance decreases it becomes more difficult to pass gases into and out of the lungs, decreasing flow. For example, when a patient is intubated, i.e., having either an endotracheal or a tracheostomy tube in place, resistance may be increased as a result of the smaller diameter of the tube over a patient's natural airway. In addition, increased resistance may be observed in patients with obstructive disorders, such as COPD, asthma, etc. Higher resistance and/or lower compliance may necessitate, inter alia, a higher inspiratory pressure setting for delivering a prescribed pressure or volume of gases.

Unlike VC, when the set inspiratory time is reached, the ventilator may initiate exhalation. Exhalation lasts from the end of inspiration until the beginning of the next inspiration. The expiratory time ($T_E$) is based on the respiratory rate set by the clinician. Upon the end of exhalation, another VC+ mandatory breath is given to the patient. By controlling target tidal volume and allowing for variable flow, VC+ allows a clinician to maintain the volume while allowing the flow and pressure targets to fluctuate.

Several different breath types may be utilized during the spontaneous mode of ventilation. In some embodiments, a continuous positive airway pressure (CPAP) breath type is utilized during the spontaneous mode of ventilation. In other embodiments, a Bilevel breath type is utilized during the spontaneous mode of ventilation. While Bilevel provides a mixed mode of ventilation (mandatory and spontaneous breaths), the BiLevel breath type allows a patient to spontaneously trigger breaths above different provided pressures. In further embodiments, volume support (VS), pressure support (PS), proportional assist (PA), or tube compensation (TC) is utilized during the spontaneous mode of ventilation.

The ventilator during a CPAP breath type maintains a continuous level of positive airway pressure throughout a breath. The CPAP breath type is functionally similar to PEEP, except that PEEP is an applied pressure against exhalation and CPAP is a pressure applied during inspiration and exhalation. Further, no additional pressure above the level of CPAP is provided. The CPAP breath type is utilized during a spontaneous mode of ventilation because a patient must initiate all of his or her breaths during the CPAP breath type.

During a Bilevel breath type, the mandatory breaths are always pressure-controlled and spontaneous breaths can be pressure-supported, PA, VS, or tube compensated. BiLevel establishes two levels of positive airway pressure, similar to having two levels of PEEP. Cycling between the two levels can be triggered by BiLevel timing settings or by patient effort. The two levels of PEEP may be referred to as $PEEP_{HIGH}$ and $PEEP_{LOW}$. At each level the Bilevel breath has a way to cycle from one PEEP level to the other, to respond to spontaneous inspirations, to calculate pressure support, to synchronize transitions between PEEP levels with the patient's breathing, and to transition into and out of BiLevel mode. Over the course of a breath interval, BiLevel cycles the ventilator between the two PEEP levels ($PEEP_{HIGH}$ and $PEEP_{LOW}$). The durations of $PEEP_{HIGH}$ and $PEEP_{LOW}$ are defined by the variables time high ($T_{HIGH}$) and a time low ($T_{LOW}$). BiLevel attempts to synchronize the transition from one PEEP level to the other with the patient's breathing pattern.

The actual durations of $T_{HIGH}$ and $T_{LOW}$ vary according to whether or not the patient makes any spontaneous inspiratory efforts. To improve ventilator-patient synchrony, BiLevel allows $T_{HIGH}$ and $T_{LOW}$ to be extended to prevent transitions to $PEEP_{LOW}$ during inspiration and to $PEEP_{HIGH}$ during early exhalation. If the patient breathes spontaneously at either PEEP level, the monitored respiratory rate increases. If the patient triggers only transitions from one PEEP level to the other, the monitored respiratory rate can increase or decrease. If the patient does not trigger any transitions between PEEP levels and does not breathe spontaneously, the monitored respiratory rate equals the set rate, and the cycle interval equals 60/E Further, during a Bilevel breath type, the spontaneous breaths can be augmented with pressure support. The Bilevel breath type allows the operator to add pressure support to breaths taken at either pressure level to offset patient circuit resistance or unload inspiratory work by augmenting tidal volume. If the pressure support level is set higher than $PEEP_{HIGH}$, the upper portion of the PS breath actually appears above the $PEEP_{HIGH}$ level. The PS breath can also be seen during $T_L$. Note that when no pressure support is set, a spontaneous effort receives a predetermined amount of pressure, such as 1.5 cmH$_2$O of pressure, to reduce the work of breathing.

The VS breath type is utilized in the present disclosure as a spontaneous breath. VS is generally used with a triggering (spontaneously breathing) patient when the patient is ready to be weaned from a ventilator or when the patient cannot do all of the work of breathing on his or her own. When the ventilator senses patient inspiratory effort, the ventilator delivers a set tidal volume during inspiration. The tidal volume may be set and adjusted by the clinician. The patient controls the rate, inspiratory flow, and has some control over the inspiratory time. The ventilator then adjusts the pressure over several breaths to achieve the set tidal volume. When the machine senses a decrease in flow, or inspiration time reaches a predetermined limit, the ventilator determines that inspiration is ending. When delivered as a spontaneous breath, exhalation in VS lasts from a determination that inspiration is ending until the ventilator senses a next patient effort to breathe.

The PS breath type is a form of assisted ventilation and is utilized in the present disclosure during a spontaneous breath. The PS breath type is a patient triggered breath and is typically used when a patient is ready to be weaned from a ventilator or for when patients are breathing spontaneously but cannot do all the work of breathing on their own. When the ventilator senses patient inspiratory effort, the ventilator provides a constant pressure during inspiration. The pressure may be set and adjusted by the clinician. The patient controls the rate, inspiratory flow, and to an extent, the inspiratory time. The ventilator delivers the set pressure and allows the flow to vary. When the machine senses a decrease in flow, or determines that inspiratory time has reached a predetermined limit, the ventilator determines that inspiration is ending. Exhalation in the PS breath type lasts from a determination that inspiration is ending until the ventilator senses a patient effort to breathe.

The PA breath type, as discussed above, refers to a type of ventilation in which the ventilator acts as an inspiratory amplifier that provides pressure support based on the patient's WOB and is describe in further detail above.

A TC breath type is similar to the PA breath type. The TC breath type delivers breathing gases to a spontaneously-breathing patient with the objective of reducing the patient's work of breathing imposed by an artificial airway. During a TC breath type, the ventilator compensates for the load associated with breathing through an endotracheal or tracheostomy tube. The TC breath type calculates a tube resistance based on the tube type (endotracheal or tracheostomy) and the tube's internal diameter, which are settings input by the clinician. A tube compensation pressure is then calculated by the ventilator during the TC breath type as a function of the patient's monitored flow, the calculated tube resistance, and a percent support setting (also known as support setting) input by the clinician. During inhalation, the ventilator during the TC breath type delivers the tube compensation pressure plus a set PEEP to the patient airway. Upon reaching an expiration sensitivity setting (or other cycling criteria), the ventilator during the TC breath type initiates exhalation. As with other pressure-based breath types, the ventilator during the TC breath type does not target a set tidal volume or flow pattern.

The exercise module 160 monitors the patient during the spontaneous mode of ventilation based on sensor output. In some embodiments, the exercise module 160 switches from the spontaneous mode of ventilation back to the set mandatory mode of ventilation when the first of the following events occur during the spontaneous mode based on the sensor output: (1) detection of patient fatigue and (2) a predetermined exercise period expires and no inspiratory triggers are detected during the exercise period. In other embodiments, the exercise module 160 switches from the spontaneous mode of ventilation back to the set mandatory mode of ventilation when the first of the following events occur during the spontaneous mode based on the sensor output: (1) detection of patient fatigue and (2) a predetermined exercise period expires. In further embodiments, the exercise module 160 switches from the spontaneous mode of ventilation back to the set mandatory mode of ventilation when the first of the following events occur during the spontaneous mode based on the sensor output: (1) detection of a trend towards patient fatigue and (2) a predetermined exercise period expires and no inspiratory triggers are detected during the exercise period. In other embodiments, the exercise module 160 switches from the spontaneous mode of ventilation back to the set mandatory mode of ventilation when the first of the following events occur during the spontaneous mode based on the sensor output: (1) detection of a trend towards patient fatigue and (2) a predetermined exercise period expires.

The detection of patient fatigue by the ventilator 100 is discussed above. The ventilator utilizes the fatigue module 117 and baseline module 118 as described above to detect patient fatigue. Further, the ventilator 100 may further utilize the indicator module 119 to detect patient fatigue as described above. In some embodiments, at least one of the fatigue indicators utilized to detect fatigue is WOB. The detection of a trend toward patient fatigue is determined by the ventilator 100 when two or more consecutive changes of a fatigue indicator received from the baseline module 118 that do not breach the fatigue threshold get consecutively closer to breaching the fatigue threshold.

There are several different trigger types or systems and/or methods utilized by the ventilator 100 for detecting patient triggers and/or cycles. In some embodiments, the trigger type for detecting patient effort may be selected or input by an operator. In some embodiments, the trigger type is automatically selected by the ventilator. Any suitable type of triggering detection for determining a patient trigger may be utilized by the ventilator, such as nasal detection, diaphragm detection, and/or brain signal detection. Further, the ventilator may detect patient triggering via a pressure-monitoring method, a flow-monitoring method, direct or indirect measurement of neuromuscular signals, or any other suitable method. Sensors 107 suitable for this detection may include any suitable sensing device as known by a person of skill in the art for a ventilator. In addition, the sensitivity of the ventilator to changes in pressure and/or flow may be adjusted such that the ventilator may properly detect the patient effort, i.e., the lower the pressure or flow change setting the more sensitive the ventilator may be to patient triggering.

According to embodiments, a pressure-triggering method may involve the ventilator monitoring the circuit pressure, as described above, and detecting a slight drop in circuit pressure. The slight drop in circuit pressure may indicate that the patient's respiratory muscles, are creating a slight negative pressure gradient between the patient's lungs and the airway opening in an effort to inspire. The ventilator may interpret the slight drop in circuit pressure as patient effort and may consequently initiate inspiration by delivering respiratory gases.

Alternatively, the ventilator may detect a flow-triggered event. Specifically, the ventilator may monitor the circuit flow, as described above. If the ventilator detects a slight drop in flow during exhalation, this may indicate, again, that the patient is attempting to inspire. In this case, the ventilator is detecting a drop in bias flow (or baseline flow) attributable to a slight redirection of gases into the patient's lungs (in response to a slightly negative pressure gradient as discussed above). Bias flow refers to a constant flow existing in the circuit during exhalation that enables the ventilator to detect expiratory flow changes and patient triggering. For example, while gases are generally flowing out of the patient's lungs during exhalation, a drop in flow may occur as some gas is redirected and flows into the lungs in response to the slightly negative pressure gradient between the patient's lungs and the body's surface. Thus, when the ventilator detects a slight drop in flow below the bias flow by a predetermined threshold amount (e.g., 2 L/min below bias flow), it may interpret the drop as a patient trigger and may consequently initiate inspiration by delivering respiratory gases.

The predetermined exercise period begins at the start of spontaneous ventilation. In some embodiments the predetermined exercise period is determined by the ventilator. In other embodiments, the predetermined exercise period is selected or input by a clinician. In some embodiments, the predetermined exercise period is about 1 minute, 2 minutes, 3 minutes, 4 minutes, 5 minutes, 6 minutes, 7 minutes, 8 minutes, 9 minutes, or 10 minutes. However, the predetermined exercise time may be any suitable time frame for providing the patent with an opportunity to spontaneously trigger a breath to provide the diaphragm of the patient with some exercise. However, the exercise period should not be so long that the exercise period deprives a non-triggering patient of necessary ventilation.

As discussed above, in some embodiments, the ventilator 100 includes an oxygen module 164. In some embodiments, the oxygen module 164 automatically increases a fractionally inspired oxygen ($FiO_2$) and/or positive end expiratory pressure (PEEP) delivered to the patient during the exercise period. In other embodiments, the oxygen module monitors $SpO_2$ during the exercise period. If the oxygen module 164 determines a drop in $SpO_2$ during the exercise period, the oxygen module 164 determines that the pneumatic system 102 of the ventilator 100 needs to deliver more oxygen to the patient. If the oxygen module 164 determines that $SpO_2$ does not drop during the exercise period, then the oxygen module 164 does not send any instructions to the pneumatic system 102 of the ventilator 100. No instructions are sent to the pneumatic system 102 of the ventilator 100 by the oxygen module 164 because the current oxygen level delivered to the patient 150 is sufficient for ventilating the patient 150. In some embodiments, the oxygen module 164 increases the level of $FiO_2$ delivered to the patient by about 5%.

The notification module 115 may further display a notification relating to the mandatory mode time period, exercise period, detected triggers, oxygen threshold, mode of ventilation, breath type, detected fatigue, monitored $FiO_2$, monitored $SpO_2$, monitored PEEP, and/or any other parameter relating to the exercise of the diaphragm. For example, the notification may display that the mandatory mode time period is active, that that the exercise period is being utilized, and/or a change to the delivered oxygen. These notifications may include any of the features discussed above for a notification message, such as a hierarchical structure, display on a remote monitoring system, and/or a summarize format with recommendations offered upon selection.

In some embodiments, if the event that occurred is detected fatigue, the fatigue module 117 of the ventilator 100 confirms the detection of patient fatigue by the changing back to the previously utilized mandatory mode of ventilation. In this embodiment, the fatigue module 117 after a predetermined rest time that begins when the exercise module 160 changes from the spontaneous mode back to the previously utilized mandatory mode because patient fatigue was detected. In some embodiments, the predetermined rest time is several minutes to a few hours. For example, the predetermined rest time is about 30 minutes, 45 minutes, 1 hour, 1.25 hours, 1.5 hours, 1.75 hours, 2 hours, 3 hours, 4 hours, or 5 hours. However, any suitable amount of time to provide the patient with rest to mitigate and confirm fatigue may be utilized by the ventilator 100. The mandatory mode of ventilation provides the patient with additional ventilation support and thereby is allowing the patient to rest during the predetermined rest time.

In some embodiments, the fatigue module 117 compares the rested parameters to the breached parameters. The fatigue module 117 determines if the implemented recommendation mitigated and thereby confirmed the determined fatigue based on the comparison of the rested parameters to the breached parameters. If the fatigue module 117 determines that the rested parameters have improved by a predetermined amount from the breached parameters, then the fatigue module 117 determines that the implemented recommendation mitigated and thereby confirmed the patient fatigue. However, if the fatigue module 117 determines that the rested parameters have not improved by a predetermined amount from the breached parameters, then the fatigue module 117 determines that the implemented recommendation did not mitigate the patient fatigue and that the cause for the change in the patient may not have been related to fatigue In some embodiments, the rested parameter is considered to be improved if the rested parameter improved by 75% or more when compared to the breached parameters.

In other embodiments, the fatigue module 117 compares the rested parameters to the baseline. The fatigue module 117 determines if the mandatory mode of ventilation mitigated and thereby confirmed the determined fatigue based on the comparison of the rested parameters to the baseline. If the fatigue module 117 determines that the rested parameters have improved by a predetermined amount when compared to the baseline, then the fatigue module 117 determines that the implemented recommendation mitigated and thereby confirmed the patient fatigue. However, if the fatigue module 117 determines that the rested parameters have not improved by a predetermined amount when compared to the baseline, then the fatigue module 117 determines that the implemented recommendation did not mitigate the patient fatigue and that the cause for the change in the patient may not have been related to fatigue.

As discussed above, in some embodiments, the rested parameter is considered to be improved if the rested parameter improved by 50% or more when compared to the baseline. In some embodiments, the rested parameter is considered to be improved if the rested parameter improved by 80% or more when compared to the baseline. In other embodiments, the rested parameter is considered to be improved if the rested parameter no longer breaches the predetermined threshold for determining patient fatigue when compared to the baseline.

If the mandatory mode mitigated the fatigue of the patient, then the patient is confirmed to have been fatigued. Accordingly, as discussed above, in some embodiments, if the fatigue module 117 determines that the mandatory mode mitigated the fatigue, then the fatigue module 117 instructs the notification module 115 to display a notification relating to the mitigated fatigue.

If the mandatory mode of ventilation did not mitigate the fatigue, then the patient may not have been fatigued, the implemented recommendation may not have been sufficient to mitigate the patient fatigue, and/or the patient's event may have deteriorated. Accordingly, in some embodiments, if the fatigue module 117 determines that the implemented recommendation did not mitigate the fatigue, then the fatigue module 117 instructs the notification module 115 to display a notification relating to the unmitigated fatigue.

As discussed above, the notification module 115 displays notification relating to the unmitigated fatigue based on the instructions from the fatigue module 117. The notification includes a notification that the fatigue was not fixed by the implemented recommendation. The notification may further include a notice that the patient fatigue was an incorrect assessment, that the implemented recommendation was insufficient to mitigate the patient fatigue, and/or that the patient's condition may have deteriorated.

Figure 2:
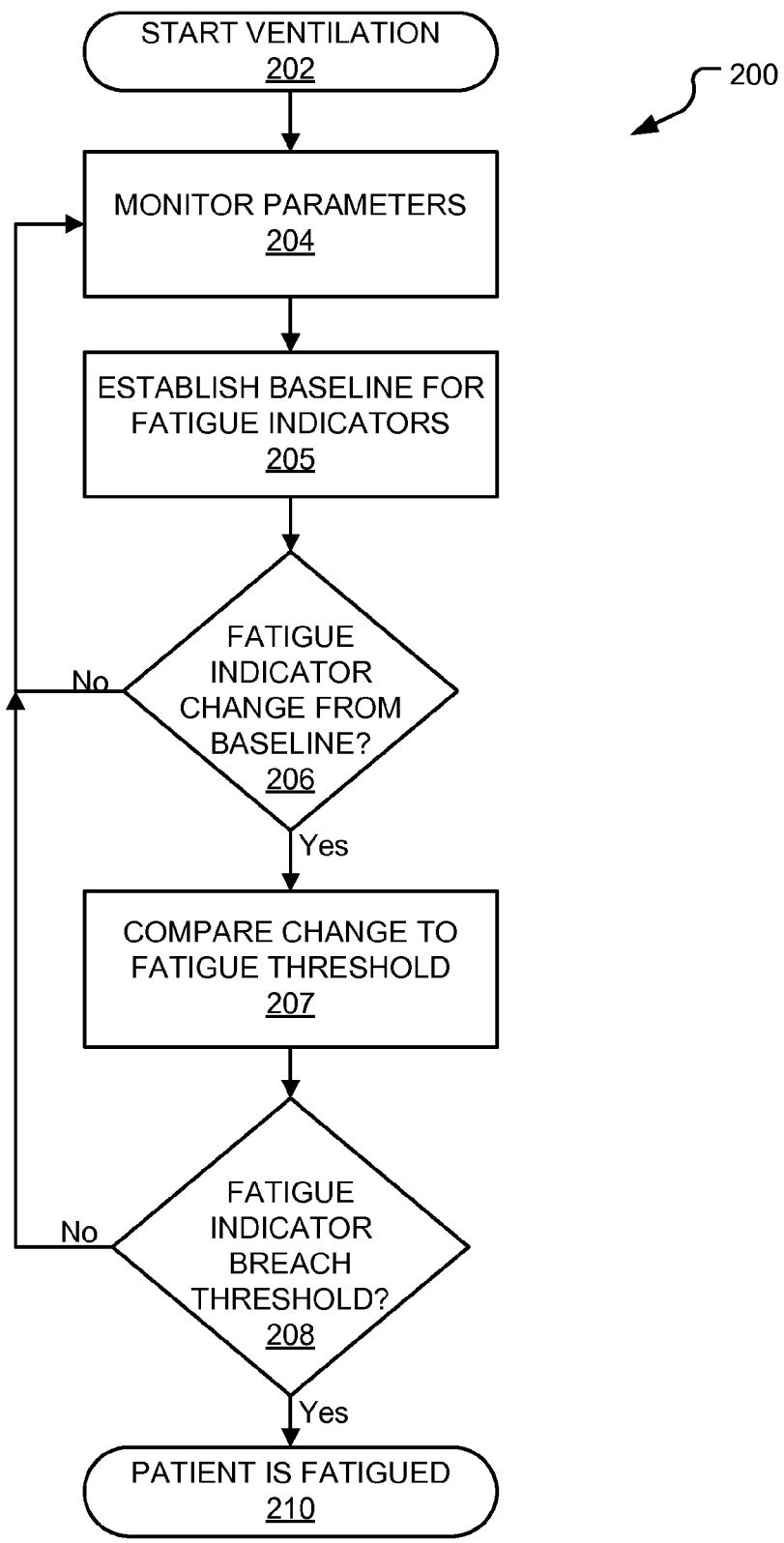
FIG. 2 illustrates an embodiment of a method for determining patient fatigue while ventilating a patient on a ventilator.

FIG. 2 illustrates an embodiment of a method 200 for ventilating a patient with a ventilator that detects patient fatigue. Current ventilators do not monitor, measure, and/or estimate the fatigue of a patient. Patient fatigue could result in longer ventilation times and worsening of the patient's condition. Accordingly, method 200 detects patient fatigue. In further embodiments, the method 200 displays a fatigue notification. In additional embodiments, method 200 automatically implements changes to the patient's ventilation to mitigate patient fatigue.

As illustrated, method 200 is performed after the start of ventilation 202. The ventilator ventilates the patient based on selected/input parameters, such as breath type, height, and/or weight. Once ventilation has begun 202, the ventilation performs a monitoring operation 204.

Method 200 includes a monitoring operation 204. During the monitoring operation 204, the ventilator monitors one or more parameters. In some embodiments, the parameters are fatigue indicators. In some embodiments, the parameters include inspiratory lung flow, net lung flow, airway pressure, $PaCO_2$, $VCO_2$, $E_{di}$, $P_{di}$, $P_i$, cardiac output, $V_t$, diaphragm movement, $P_{esoph}$, $E_{phr}$, $SpO_2$, MV, and etc. The monitoring operation 204 may be performed by sensors and data acquisition subsystems. The sensors may include any suitable sensing device as known by a person of skill in the art for a ventilator. In some embodiments, the sensors are located in the pneumatic system, the breathing circuit, and/or on the patient. In some embodiments, the ventilator during the monitoring operation 204 monitors the parameters every computational cycle (e.g., 2 milliseconds, 5 milliseconds, 10 milliseconds, etc.). In other embodiments, the ventilator during the monitoring operation 204 monitors the parameters after a predetermined number of breaths (e.g., 1 breath, 2 breaths, 3 breaths, etc.). In other embodiments, the ventilator during the monitoring operation 204 monitors the parameters after a predetermined set sensor time period (e.g., 1 second, 2 seconds, 30 seconds, 1 minute, 5 minutes, etc.).

Further, during the monitoring operation 204, the ventilator may derive (which includes estimate) a fatigue indicator based on the sensor measurements or output. For example, the ventilator during monitoring operation 204 determines a patient WOB based on sensor output. In some embodiments, the work of breathing is calculated by entering the sensor output into the Equation of Motion. In other embodiments, the WOB of breathing is derived by inputting various measurements (also known as sensor output) from various sensors into breathing algorithms. In some embodiments, the sensor output is monitored inspiratory flow and/or net flow. In other embodiments, at least one of resistance, elastance, and/or compliance estimates derived from the sensor output is utilized to determine the WOB of the patient. However, any known systems or methods for calculating a WOB of the patient from sensor output may be utilized. For example, methods exist that calculate work of breathing from sensors attached to the body to detect neural or muscular activity as well as methods that determine a work of breathing based on respiratory flow, respiratory pressure or a combination of both flow and pressure. For example, in one embodiment, the WOB of the patient is calculated with the following equation: $WOB = \int Pressure \times Volume$.

Other fatigue indicators may need to be derived (which includes estimated) from the monitored parameters. Accordingly, the ventilator during monitoring operation 204 may further derive either fatigue indicators, such as RSBI, respiration rate, $P_{tid}$, and etc. In some embodiments, the monitored parameters are directly utilized as fatigue indicators. For example, $T_I$ and $E_{di}$ may be directly monitored by the ventilator during monitoring operation 204.

As illustrated, method 200 includes an establishing a baseline operation 205. During the establishing a baseline operation 205, the ventilator establishes a baseline for one or more fatigue indicators. The baseline designates a normal level or desired level of the fatigue indicator for the patient. The fatigue indicator is any suitable parameter for providing an indication of patient fatigue. For example, at least one of the following parameters may be utilized as the fatigue indicator: $PaCO_2$, WOB, $VCO_2$, EMG of a respiration accessory muscle, $E_{di}$, $P_{0.1}$, diaphragmatic position, $P_{di}$, $P_{di,max}$, $P_{i,max}$, cardiac output, velocity of muscle shortening, $V_t$, diaphragm movement, $P_{esoph}$, $P_{di}$ maximal relaxation rate, $P_{mus}$ maximum relation rate, abdominal and/or rib cage muscle contractions, paradoxical breathing, $V_{e\ alv}$, respiration rate, (BIS LOS), RSBI, $V_t/T_i$, $P_{di}/P_{di\ max}$, $T_i/T_{tot}$, $V_d/V_t$, $P_{tid}$ or $(Pa_{di}/P_{di\ max})/(T_i/T_{tot})$, $T_i/T_{tot} \cdot P_{di}/P_{dimax}$, respiration muscle pressure divided EMG integral, $E_{phr}$, $SpO_2$, MV, and/or $P_{mus}$. This list exemplary only and is not meant to limit the disclosure. In an alternative embodiment, the fatigue indicator is a fatigue metric. The fatigue metric is any suitable function of two or more fatigue indicators. For example, the fatigue metric may add, subtract, divide, and/or multiply two or more fatigue indicators. The fatigue metric may be any suitable mathematical relationship between two or more fatigue indicators for determining patient fatigue.

In some embodiments, the ventilator during the establishing a baseline operation 205 determines a baseline for a fatigue indicator based on input from a clinician. For example, the clinician may enter the desired baseline for the patient. This allows the clinician determine the desired baseline for a fatigue indicator. The clinician may take into account the patient's history, disease state, sex, and other factors when determining the baseline for a fatigue indicator for a patient.

In an alternative embodiment, the ventilator during the establishing a baseline operation 205 determines a baseline for fatigue indicators by averaging sensor output for each of the fatigued indicators for a predetermined amount of time. The ventilator during the establishing a baseline operation 205 adds the set of measurements or sensor output generated by the repeated sensor measurements for the predetermined amount of time and then divides the total by the number of measurements taken for determine the baseline. The predetermined time period may be any suitable amount of time to determining a normal or baseline parameter value for the patient 150. In some embodiments, the predetermined amount of time is 10 minutes, 30 minutes, 45 minutes, 1 hour, 1.5 hours, 2 hours, 6 hours, 12 hours, or 24 hours.

In further, embodiments, some fatigue parameters only exist in a finite number of states. Accordingly, for these fatigue indicators a predetermined state will be the baseline. These baselines may be predetermined and automatically configured on the ventilator. For example, absence of paradoxical breathing may be a baseline. Accordingly, the presence of paradoxical breathing is a detected change from this baseline.

In some embodiment, the predetermined amount of time starts during the establishing a baseline operation 205 after the ventilator delivers a predetermined number of breaths (e.g., 1 breath, 2 breaths, 3 breaths, 5 breaths, etc.) from the start of ventilation. In other embodiments, the predetermined amount of time begins after a set start time, such as 1 minute after the beginning of ventilation, 5 minutes after the beginning of ventilation, 10 minutes after the beginning of ventilation, 1 hour after the beginning of ventilation, or 3 hours after the beginning of ventilation.

For example, in some implementations, the following may be utilized as baselines for the following fatigue indicators:

$PaCO_2$ is 38-42 mmHg;
$PaCO_2$ for patients with COPD 42-62 mmHg;
pH of 7.38-7.42;
$VCO_2$ of 180-200 mL/min;
$VCO_2$ of 2.5-3.5 mL/Kg/min;
$P_{0.1}$ of 1-2 $cmH_2O$;
$P_{di,max}$ is about 80 $cmH_2O$;
$P_{i,max}$ is about 80 $cmH_2O$;
$V_t$ is 5-6 mL/kg;
$P_{esoph}$ is 3-5 $cmH_2O$;
no paradoxical breathing;
respiration rate is 12-16/min for adults;
RSBI is less than 40;
$P_{di}/P_{di\,max}$ is around 5-10%;
$T_i/T_{tot}$ is about 30%; and
$V_d/V_t$ is 0.2-0.3.

Further, method 200 includes a change decision operation 206. The ventilator during the change decision operation 206 determines a change from the baseline based on the monitored fatigue indicators. A change is determined by the ventilator during change decision operation 206 when the current sensor output or monitor fatigue parameter is not equivalent or substantially equivalent to the baseline. In some embodiments, a fatigue parameter is considered substantially equivalent to the baseline when the difference between the fatigue parameter and the baseline is less than 1%. In other embodiments, a fatigue parameter is considered substantially equivalent to the baseline when the difference between the fatigue parameter and the baseline is less than 3%. In further embodiments, a fatigue parameter is considered substantially equivalent to the baseline when the difference between the fatigue parameter and the baseline is less than 5%.

Next, method 200 includes a fatigue comparing operation 207. The ventilator during the fatigue comparing operation 207 compares a detected change to a fatigue threshold. The fatigue threshold is any suitable fatigue indicator threshold for providing an indication of patient fatigue. In embodiments, the fatigue indicator threshold is a threshold for a fatigue metric. In some embodiments, the fatigue indicator threshold is a detected rate of change in a fatigue indicator and/or metric. In some embodiments, the fatigue threshold is at least one of the following thresholds:

work of breathing decrease below the baseline;
work of breathing increases above the baseline followed by a decrease below the baseline;
$PaCO_2$ increases from the baseline;
$VCO_2$ decreases from the baseline;
EMG of an accessory muscle indicates use of the accessory muscle;
$E_{di}$ decreases from the baseline;
$P_{0.1}$ increases and then decreases from the baseline;
diaphragmatic position becomes flattened;
$P_{di}$ decreases from the baseline;
$P_{di,max}$ decreases from the baseline;
$P_{i,max}$ decreases from the baseline;
cardiac output does not increase from the baseline with an increasing load,
velocity of muscle shortening decreases from the baseline;
EMG time domain decreases from the baseline;
EMG, frequency domain decreases from the baseline;
$V_t$ decreases from the baseline;
diaphragm movement imaging shows reduced movement from the baseline;
$P_{esoph}$ decreases from the baseline;
$P_{di}$ Maximum Relaxation Rate decreases from the baseline;
$P_{mus}$ Maximum Relaxation Rate decreases from the baseline;
alternating abdominal/rib cage muscle contractions occur or increase in frequency from the baseline;
$V_{e\,alv}$ decreases from the baseline;
respiration rate increases followed by a decrease from the baseline;
BIS LOS is normal;
RSBI increases from the baseline;
$V_t/T_i$ decreases from the baseline;
$P_{di}/P_{di\,max}$ increases from the baseline;
$T_i/T_{tot}$ increases from the baseline;
$V_d/V_t$ increases from the baseline;
$P_{tid}$ increases from the baseline;
$T_i/T_{tot}/P_{di}/P_{dimax}$ increases from the baseline; Respiration muscle pressure/EMG integral decreases from the baseline;
$E_{di}$ increases while $E_{phr}$ increases and $P_{di}$ decreases from the baseline;
$P_{di,max}$ decreases from the baseline;
$P_{i,max}$ decreases from the baseline;
$E_{di}$ increases and at least one of a decrease in $V_t$, a decrease in $VCO_2$, a decrease in $SpO_2$, an increase in $P_{0.1}$, and a decrease in MV from the baseline occurs;
$P_{mus}$ decreases and at least one of a decrease in $V_t$, a decrease in $VCO_2$, a decrease in $SpO_2$, and a decrease in MV from the baseline occurs;
$PaCO_2$ increases from the baseline by at least 10 mmHg,
$VCO_2$ decrease from the baseline by more than 20%,
$E_{di}$ decreases from the baseline by at least 25%,
$E_{di}$ stays the same while the velocity of muscle shortening decreases from the baseline;
$P_{0.1}$ increases above 4 cm of $H_2O$ and then decreases by at least 2 cm of $H_2O$,
$P_{di}$ decreases by at least 10% from the baseline;
$P_{di,max}$ decreases by at least 20% from the baseline;
$P_{i,max}$ decreases by at least 20% from the baseline;
velocity of muscle shortening decreases by at least 25% from the baseline;
EMG time domain is less than 50 uV;
EMG, frequency domain decreases by more than 20% from the baseline;
$V_t$ is below 4 mL/kg;
$P_{esoph}$ decreases by at least 10% from the baseline;
$P_{di}$ Maximum Relaxation Rate decreases by at least 20% from the baseline;
$P_{mus}$ Maximum Relaxation Rate decreases by at least 20% from the baseline;
presence of paradoxical breathing;
$V_{e\,alv}$ decreases by at least 20% from the baseline;
respiration rate increases above 35 breaths a minute;
respiration rate increases by at least 25% from the baseline followed by a decrease;
RSBI increases above 105;
$V_t/T_i$ decreases by 30% from the baseline;
$P_{di}/P_{di\,max}$ is above 40% from the baseline;
$T_i/T_{tot}$ is greater than 40% from the baseline;

$V_d/V_t$ increases by 20% from the baseline;
$V_d/V_t$ is greater than 40% from the baseline;
$P_{tid}$ increases above 0.15; and
$T_i/T_{tot}/P_{di}/P_{dimax}$ is greater than 40% from the baseline.
This list exemplary only and is not meant to limit the disclosure. Any suitable thresholds for determining fatigue in a patient during ventilation may be utilized by the ventilator.

Method 200 also includes a fatigue determining operation 208. The ventilator during the fatigue determining operation 208 determines if a detected change breaches a fatigue threshold. If the ventilator during the fatigue determining operation 208 determines that one or more detected changes breach their corresponding fatigue thresholds, the ventilator determines that the patient is fatigued 210. If the ventilator during the fatigue determining operation 208 determines that one or more detected changes do not breach the fatigue threshold, the ventilator determines that the patient is not fatigued and continues to perform monitoring operation 204.

In some embodiments, the ventilator during the fatigue determining operation 208 monitors numerous fatigue indicators to determine if any changes of the fatigue indicators breach their corresponding fatigue thresholds. In alternative embodiments, the ventilator during the fatigue determining operation 208 monitors numerous fatigue indicators to determine if a predetermined number or a select group of the fatigue indicators have changed to breach their corresponding fatigue threshold. In other embodiments, the ventilator during the fatigue determining operation 208 monitors only one predetermined fatigue indicator to determine if a change in that predetermined fatigue indicator breaches the corresponding fatigue threshold.

In additional embodiments, the ventilator during the fatigue comparing operation 207 and/or fatigue determining operation 208 may determine the level of fatigue detected. To determine the level of fatigue detected, the ventilator during the fatigue comparing operation 207 and/or fatigue determining operation 208 may weigh how much how much a fatigue threshold was breached, by how many fatigue thresholds were breached, and/or a rate at which any breach is increasing. The ventilator during the fatigue comparing operation 207 and/or fatigue determining operation 208 may utilize a mathematical algorithm for weighing the above parameters to determine the level of fatigue detected. In some embodiments, the ventilator determines the patient fatigue as high, medium, or low. In other embodiments, a fatigue index is determined by the ventilator during the fatigue comparing operation 207 and/or fatigue determining operation 208. The fatigue index may indicate the level of fatigue experienced by the patient. For example, the fatigue index may be a scale of 1-10 or 1-3. The higher the degree of patient fatigue, the higher the fatigue index listed by the ventilator (1 may be the high end or 10 and 3 may be the high end of the scale depending upon the desired index). The listed fatigue index is above are not meant to be limiting. Any suitable indication of a patient's fatigue level may be utilized by the ventilator during the fatigue comparing operation 207 and/or fatigue determining operation 208 as the fatigue index, including symbols, colors (i.e., red, yellow, and green to designate different fatigue levels), text, numbers, and/or animations.

Figure 3A:
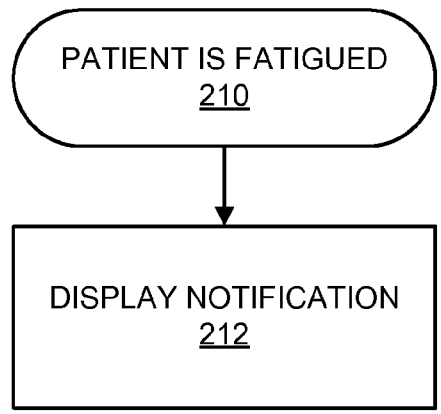
FIG. 3A illustrates an embodiment of a method for notifying a clinician of patient fatigue during ventilation.

In some embodiments, method 200 includes a displaying operation 212 as illustrated in FIG. 3A. FIG. 3A illustrates an embodiment of a method for notifying a clinician of patient fatigue during ventilation. During displaying operation 212, the ventilator after patient fatigue is detected 210, displays a fatigue notification message. The ventilator during displaying operation 212 determines an appropriate notification based on the fatigue comparing operation 207 and/or fatigue determining operation 208. When patient fatigue is implicated, many clinicians may not be aware of adjustments to parameters that may reduce or eliminate fatigue. As such, upon detection of patient fatigue, the ventilator during displaying operation 212 may notify the clinician that patient fatigue is implicated and/or provide recommendations to the clinician for mitigating patient fatigue. Accordingly, the notification message may include a recommendation for mitigating patient fatigue. For example, ventilator during displaying operation 212 may notify the clinician by displaying a notification on a display and/or within a window of the GUI. According to additional embodiments, the notification is communicated to and/or displayed on a remote monitoring system. According to alternative embodiments, the notification is any audio and/or visual notification.

In order to accomplish the various aspects of the notification message display, the ventilator during displaying operation 212 may communicate with various ventilator components or modules. That is, the ventilator during displaying operation 212 may receive an indication that the patient is fatigued by any suitable means. In addition, the ventilator during displaying operation 212 may receive information regarding one or more parameters that implicated the presence of patient fatigue and information regarding the patient's ventilator settings and treatment. Further, according to some embodiments, the ventilator during displaying operation 212 may have access to a patient's diagnostic information (e.g., regarding whether the patient has ARDS, COPD, asthma, emphysema, or any other disease, disorder, or condition).

In some embodiments, notifications determined by ventilator during displaying operation 212 may be provided according to a hierarchical structure such that a notification may be initially presented in summarized form and, upon clinician selection, an additional detailed notification may be displayed. According to alternative embodiments, a notification determined by ventilator during displaying operation 212 is initially presented without a recommendation and, upon clinician selection, a recommendation message is displayed. Alternatively or additionally, the notification determined by ventilator during displaying operation 212 simultaneously displays a detection of patient fatigue with a recommendation message in any suitable format or configuration.

Specifically, according to some embodiments, the notification alerts the clinician as to the detection of a fatigue, a change in a patient's fatigue, or an effectiveness of ventilator treatment of patient fatigue. For example, the notification message determined by ventilator during displaying operation 212 may alert the clinician that fatigue has been detected and the parameters that indicated the patient fatigue (i.e., WOB, RSBI, $V_t$, $E_{di}$, and etc.). The notification may further alert the clinician regarding the particular breach or level of breach of the particulars parameter(s) that implicated patient fatigue (e.g., WOB, cardiac output, $P_{di}$, $VCO_2$, etc.) For example, the notification may recite that patient fatigue is detected and then list the WOB measurements that indicated the patient fatigue.

In some embodiments, the notification recites the following messages:
 fatigue detected;
 fatigue warning;
 fatigue implicated; and
 fatigue notification.
In some embodiments, the notification may further recite the one or more fatigue indicator measurements that indicated the patient fatigue. In other embodiments, the notification may also recite the one or more fatigue thresholds.

In other embodiments, the level of fatigue is displayed in the notification by the ventilator during displaying operation 212. For example, the notification may list that a high, medium, or low level of patient fatigue is detected. In other embodiments, a fatigue index may be listed in the notification. As discussed above the fatigue index may indicate the level of patent fatigue as determined by ventilator.

Additionally, according to embodiments as discussed above, the notification may provide various suggestions to the clinician for addressing detected patient fatigue. According to additional embodiments, the notification may be based on the particular parameter(s) that implicated the patient fatigue. Additionally or alternatively, the recommendation may be based on current ventilator settings (e.g., breath type). Additionally or alternatively, the recommendation may be based on a diagnosis and/or other patient attributes. Further still, the recommendation may include a primary recommendation message and a secondary recommendation message. For example, the primary recommendation message may recite, "consider switching breath types" and the secondary recommendation message may recite, "consider switching to VC+ breath type." In another example, the primary recommendation message may recite, "consider utilizing a basal level of pressure support in the PA breath" and the secondary recommendation may recite, "consider utilizing 5 cm H$_2$O as your basal level of support."

The ventilator during displaying operation 212 may generate a notification via any suitable method or system. For example, the notification may be provided as a tab, banner, dialog box, or other similar type of display. Further, the notification may be provided along a border of the graphical user interface, near an alarm display or bar, or in any other suitable location. A shape and size of the notification may further be optimized for easy viewing with minimal interference to other ventilator displays. The notification message may be further configured with a combination of icons and text such that the clinician may readily identify the message as a notification message.

The ventilator during displaying operation 212 may generate one or more recommendations via any suitable systems or methods. The one or more recommendations may provide suggestions and information regarding addressing the detected patient fatigue. In some embodiments, the one or more recommendations identifies the parameters that implicated the detected condition, provides suggestions for adjusting the one or more parameters to address the detected fatigue, provides suggestions for checking ventilator equipment or patient position, and/or provides other helpful information. For example, if fatigue is implicated, the notification may include one or more of the following recommendations:

consider switching to invasive ventilation;
consider switching to a negative feedback breath type;
consider switching to a PS, PC, VC, or VS breath type;
consider increasing ventilation support;
consider increasing support setting in the PA breath type;
consider increasing support setting in the DEA breath type;
consider increasing support setting in a positive feedback breath type;
consider increasing set respiratory rate;
consider utilizing a basal level of support in the PA breath type;
consider utilizing a basal level of support in the DEA breath type; and
consider utilizing a basal level of support in a positive feedback breath type.

This list of recommendations is exemplary only. Any suitable recommendation for increasing the ventilator support of the patient may be utilized as a recommendation to mitigate patient fatigue.

As discussed above, in some embodiments, after patient fatigue is detected by the ventilator during the fatigue determining operation 208, the ventilator during displaying operation 212 recommends switching from non-invasive ventilation to invasive ventilation. Studies have shown that waiting too long before switching from a non-invasive ventilation to invasive ventilation when a patient is responding poorly to ventilation (e.g., detecting patient fatigue) has been linked to an increased mortality rate. Accordingly, if patient fatigue is detected by ventilator during the fatigue determining operation 208, the ventilator during displaying operation 212 may recommend switching from non-invasive ventilation (i.e., using a nasal mask and other settings) to invasive ventilation (i.e., using an endotracheal tube and other settings).

Figure 3B:
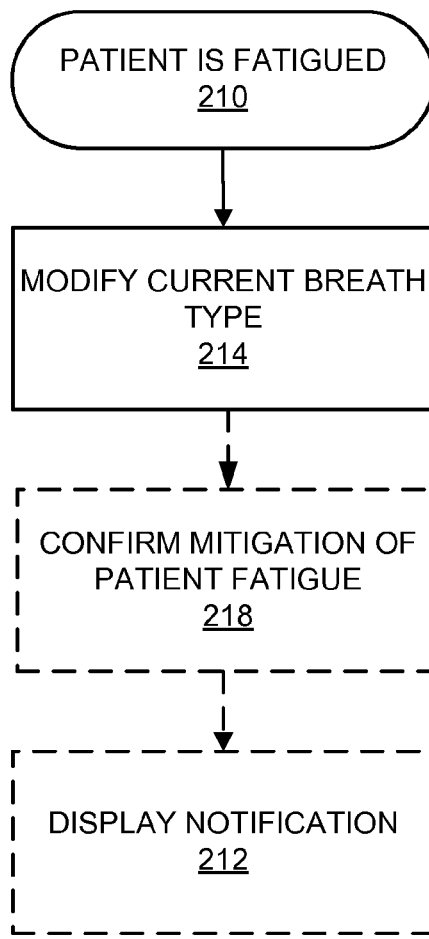
FIG. 3B illustrates an embodiment of a method for managing patient fatigue during ventilation.

In some embodiments when a positive feedback breath type is being utilized by the ventilator, method 200 includes a modifying breath type operation 214 as illustrated in FIG. 3B. FIG. 3B illustrates an embodiment of a method for managing patient fatigue during ventilation. In some embodiments, during the modifying breath type operation 214, the ventilator after patient fatigue is detected 210 modifies the positive feedback breath type by increasing the support setting, which increases the level of pressure support provided by the positive feedback breath type. In other embodiments, during the modifying breath type operation 214, the ventilator after patient fatigue is detected 210 modifies the positive feedback breath type to provide a basal level of pressure support. With positive feedback algorithms, the amount of support provided by the ventilator is proportional to the monitored patient's work of breathing. However, if a patient becomes fatigued, the patient may decrease their work of breathing. In positive feedback breath types, support is withdrawn as the patient decreases his or her work of breathing. Therefore, the patient receives less support as the patient become more fatigued, which may cause the patient's fatigue to worsen. Accordingly, the basal level of pressure support is a set pressure, pressure level, or support setting that provides the minimum amount of pressure support that the positive feedback breath type delivers regardless of the patient derived WOB. Accordingly, the basal level of pressure support limits the positive feedback from reducing support beyond a predetermined threshold. Therefore, the patient receives this minimal amount of pressure support in an attempt to mitigate the detected patient fatigue. In one embodiment, the positive feedback breath type is a PA breath type. In another embodiment, the positive feedback breath type is a DEA breath type. In some embodiments, the ventilator performs the modifying breath type operation 214 and the displaying operation 212 concurrently.

Figure 3C:
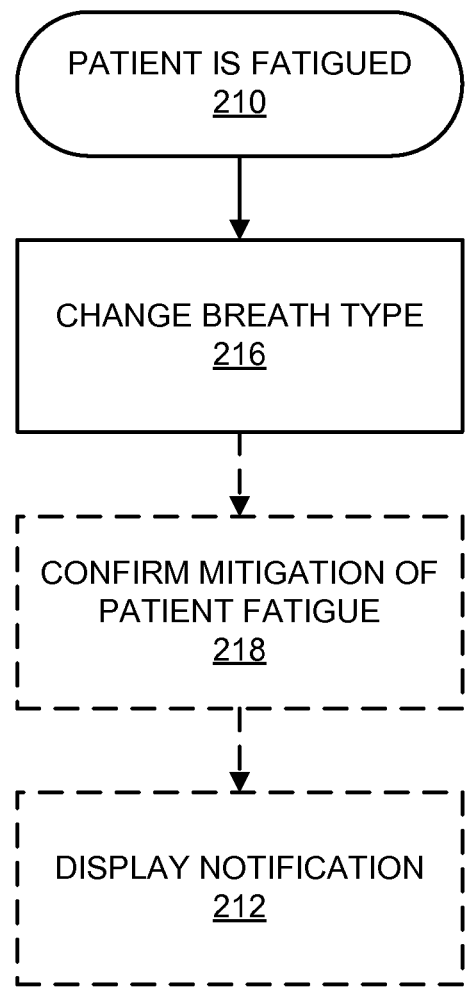
FIG. 3C illustrates an embodiment of a method for managing patient fatigue during ventilation.

In some embodiments when a positive feedback breath type is being utilized by the ventilator, method 200 includes a changing breath type operation 216 as illustrated in FIG. 3C. FIG. 3C illustrates an embodiment of a method for managing patient fatigue during ventilation. During the changing breath type operation 216, the ventilator after patient fatigue is detected 210, switches from the positive feedback breath type to a non-positive feedback breath type. For example, the ventilator during the changing breath type operation 216 may switch to a negative feedback breath type (e.g., VS or VC+) or to another breath type (e.g., VC, VS, and PC). The change in breath type prevents a fatigued patient from receiving less support with each increasing degree of fatigue. In some embodiments, the ventilator performs the changing breath type operation 216 and the displaying operation 212 concurrently.

Figure 4:
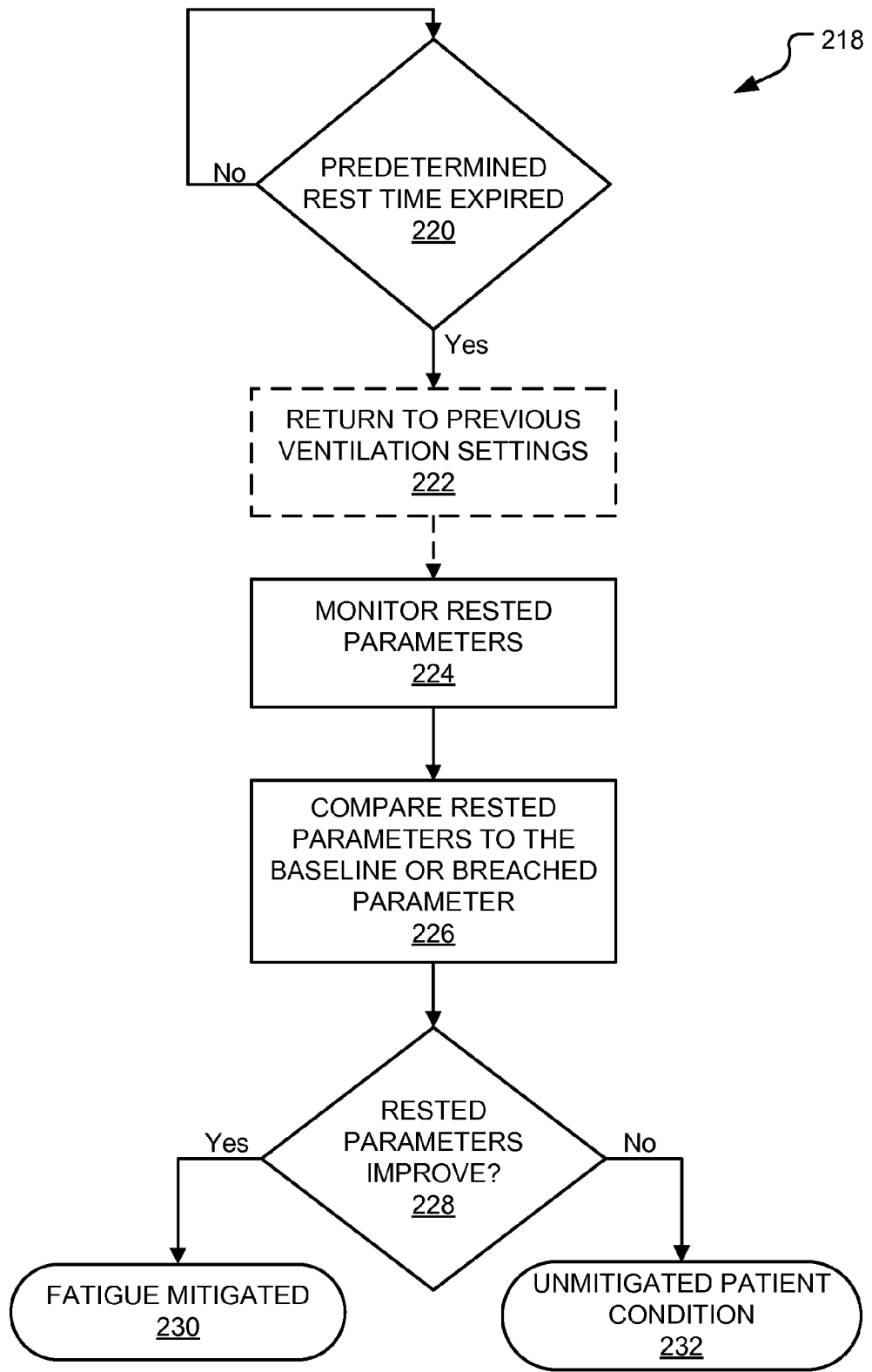
FIG. 4 illustrates an embodiment of a method for determining if an implemented recommendation mitigated patient fatigue.

In additional embodiments, method 200 includes a confirming operation 218. The confirming operation 218 may be performed by the ventilator after the ventilator performs the modifying breath type operation 214 or the changing breath type operation 216 as illustrated in FIGS. 3B and 3C. The confirming operation 218 determines if the detected patient fatigue 210 was mitigated by performance of the modifying breath type operation 214 or the changing breath type operation 216. The confirming operation 218 includes a rest time determining operation 220, a rest monitoring operation 224, a rest comparing operation 226, and an improvement determining operation 228 as illustrated in FIG. 4. FIG. 4 illustrates an embodiment of a method for determining if an implemented recommendation mitigated patient fatigue. Accordingly, as discussed with reference to confirming operation 218, referring to implementing a recommendation refers to the modifying breath type operation 214 and/or the changing breath type operation 216.

The ventilator during the rest time determining operation 220 determines if a predetermined rest time has expired. In some embodiments, the predetermined rest time is selected by the operator. In other embodiments, the predetermined rest time is determined by the ventilator. The implemented recommendation, such as the modified breath type or the changed breath type, provides the patient with additional ventilation support and thereby allows the patient to rest during the predetermined rest time. Accordingly, the predetermined rest time begins when the recommendation is implemented. If the ventilator during the rest time determining operation 220 determines that the predetermined rest time has expired, the ventilator selects to perform rest monitoring operation 224. If the ventilator during the rest time determining operation 220 determines that the predetermined rest time has not expired, the ventilator selects to re-perform the rest time determining operation 220. In some embodiments, when the ventilator during the rest time determining operation 220 determines that the predetermined rest time has expired, the ventilator selects to perform a return setting operation 222 prior to performing the rest monitoring operation 224.

The ventilator during the return setting operation 222 changes the ventilator settings back to the ventilator settings that were utilized to ventilate the patient during the fatigue detection. For example, if the patient is currently being ventilated with a negative feedback breath type, but was being ventilated with a positive feedback breath type during the detection of the fatigue, the ventilator during the return setting operation 222 switches the breath type back to the previously utilized positive feedback breath type and associated settings. The settings are returned to the settings utilized during fatigue detection to ensure that any difference between the rested parameters and the baseline cannot be attributed to the different ventilator settings utilized during ventilation of the patient at the time of measurement.

The ventilator during the rest monitoring operation 224 monitors for rested parameters. As discussed above, rested parameters are the one or more fatigue indicators of the patient determined after the predetermined rest time. The rest monitoring operation 224 is similar to the monitoring operation 204 described above other than rest monitoring operation 224 is performed specifically after the predetermined rest time expires. Accordingly, the above description of the monitoring operation 204 applies to the rest monitoring operation 224.

In some embodiments, the ventilator during the rest comparing operation 226 compares the rested parameters to the baseline. The ventilator determines the rested parameters during the performance of the rest monitoring operation 224. The baseline, as discussed above, designates a normal level or desired level of the fatigue indicator for the patient. In some embodiments, the clinician inputs the baseline. This allows the clinician determine the desired baseline for a fatigue indicator. In an alternative embodiment, the ventilator determines a baseline for fatigue indicators by averaging sensor output for each of the fatigued indicators for a predetermined amount of time. In further, embodiments, some fatigue parameters only exist in a finite number of states. Accordingly, for these fatigue indicators a predetermined state will be the baseline. These baselines may be predetermined and automatically configured on the ventilator. For example, absence of paradoxical breathing may be a baseline. Accordingly, the presence of paradoxical breathing is a detected change from this baseline.

In other embodiments, the ventilator during the rest comparing operation 226 compares the rested parameters to the breached parameter. The ventilator determines the rested parameters during the performance of the monitoring operation 204. The breached parameters, as discussed above are the one or more fatigue indicator of the patient that breached a threshold to indicate the detected patient fatigue 210. Accordingly, ventilator determines the breached parameters during the performance of the monitoring operation 204.

Next, the ventilator during the improvement determining operation 228 determines if the rested parameters have improved when compared to the baseline. In some embodiments, the rested parameters are considered to have improved if the rested parameter improved by 80% or more when compared to the baseline. In some embodiments, the rested parameters are considered to have improved if the rested parameter improved by 95% or more when compared to the baseline. In other embodiments, the rested parameter is considered to be improved if the rested parameter no longer breaches the predetermined threshold for determining patient fatigue when compared to the baseline. In other embodiments, the rested parameter is considered to be improved if the rested parameter has improved so that the rested parameter is within 5% of the baseline. If the ventilator during improvement determining operation 228 determines that the rested parameters have improved compared to the baseline, then the patient fatigue has been mitigated 230. If the rested parameters have improved, then the implemented recommendation has allowed the patient to rest and reduced or mitigated the patient's fatigue 230 and confirmed the fatigue detection by the ventilator. If the ventilator during improvement determining operation 228 determines that the rested parameters have not improved compared to the baseline, then the patient's condition has not been mitigated 232. If the rested parameters have not improved, then the implemented recommendation has either not allowed the patient to rest enough to reduce or mitigate the patient's detected fatigue 210, something else besides patient fatigue that mimics the symptoms of patient fatigue is affecting the patient, and/or the patient's condition may have deteriorated.

In some embodiments, the displaying operation 212 is performed after the confirming step. The ventilator after determining that patient fatigue is mitigated 230, displays a fatigue mitigation notification message during displaying operation 212. The ventilator after determining that the patient fatigue is unmitigated 232, displays an unmitigated patient condition notification message during displaying operation 212. The notification displayed by the displaying operation 212 is similar to the notification described above and therefore may exhibit any of the features described above for a notification message, such as a hierarchical structure, display on a remote monitoring system, and/or a summarize format with recommendations offered upon selection.

The notification after the ventilator determined mitigated fatigue 230 may include a notification that the fatigue was fixed by the implemented recommendation. The notification after the ventilator determined mitigated fatigue 230 may further include a notice that the patient fatigue was the correct assessment, that the implemented recommendation was sufficient to mitigate the patient fatigue, and/or that the patient's condition is improved. In some embodiments, the notification after the ventilator determined mitigated fatigue 230 may further include one or more recommendations for ventilating the patient now that the patient is no longer fatigued. In further embodiments, the notification after the ventilator determined mitigated fatigue 230 may further include a reference to the rested parameters, the breached parameters, and/or the predetermined thresholds of the breached parameters. For example, the notification after the ventilator determined mitigated fatigue 230 may include:

Fatigue mitigated;
Consider switching to a positive feedback breath type;
Patient fatigue confirmed;
Fatigue reduced by at least 95%; and
etc.

The notification after the ventilator determines that the patient fatigue is unmitigated 232 may include a notification that the fatigue was not fixed by the implemented recommendation. The notification after the ventilator determines that the patient fatigue is unmitigated 232 may further include a notice that the patient fatigue was an incorrect assessment, that the implemented recommendation was insufficient to mitigate the patient fatigue, and/or that the patient's condition may have deteriorated. In some embodiments, the notification after the ventilator determines that the patient fatigue is unmitigated 232 may further include one or more recommendations for dealing with the unmitigated fatigue. In further embodiments, the notification after the ventilator determines that the patient fatigue is unmitigated 232 may further include a reference to the rested parameters, the breached parameters, and/or the predetermined thresholds of the breached parameters. For example, the notification relating to the unmitigated fatigue may include:

Fatigue treatment failed;
Patient condition deteriorating-Fatigue unmitigated;
Warning patient not responding to fatigue treatment;
Warning patient not fatigued, consider checking other causes of a low work of breathing;
Warning fatigue detected in error, consider checking other parameters to determine the cause of the patient's detected negative condition; and
etc.

In some embodiments, a microprocessor-based ventilator that accesses a computer-readable medium having computer-executable instructions for performing the method of ventilating a patient with a ventilator is disclosed. This method includes repeatedly performing the steps disclosed in method 200 above and/or as illustrated in FIG. 2, 3A, 3B, and/or 3C.

In some embodiments, the ventilator system includes: means for monitoring a plurality of fatigue indicators; means for establishing a baseline for the fatigue indicators; means for determining a change from the baseline based on the monitored fatigue indicators; means for comparing the change to a fatigue threshold; means for detecting respiratory fatigue based on the step of comparing the change to the fatigue threshold; and means for displaying a fatigue notification after the step of detecting respiratory fatigue.

Figure 5:
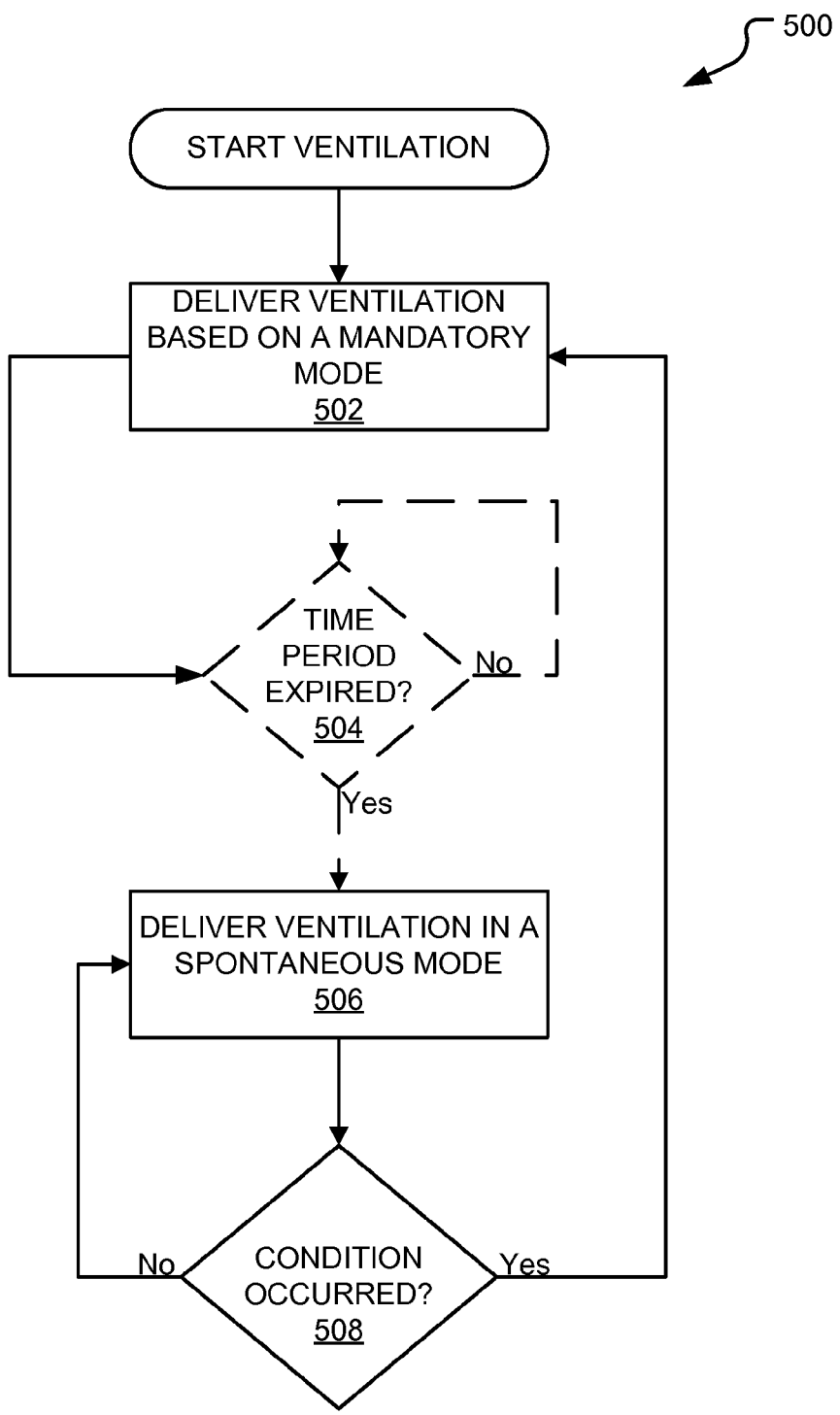
FIG. 5 illustrates an embodiment of a method for ventilating a patient on a ventilator.

FIG. 5 illustrates an embodiment of a method 500 for ventilating a patient on a ventilator. As discussed above, patients that are ventilated for an extended period of time in a mandatory mode of ventilation may develop diaphragmatic weakness or fatigue. The non-use of the diaphragm for the extended period of time during the mandatory mode may lead to diaphragm atrophy causing the diaphragmatic weakness. Accordingly, method 500 exercises the diaphragm of the patient in an attempt to mitigate or prevent the diaphragm atrophy and/or weakness. Method 500 begins after the start of ventilation.

In some embodiments, method 500 is performed or activated based on clinician input. In other embodiments, method 500 is activated after a patient has been ventilated based on a mandatory mode of ventilation for a certain amount of time. The certain amount of mandatory mode time may be input by the clinician or predetermined by the ventilator.

As illustrated, method 500 includes a mandatory mode operation 502. The ventilator during the mandatory mode operation 502 ventilates a patient based on a set mandatory mode. In some embodiments, the set mandatory mode is selected or input by an operator. In other embodiments, the set mandatory mode is determined by the ventilator. Several different breath types may be utilized during the mandatory mode. For example, a PC, VC, or VC+ breath type may be utilized during the mandatory mode. As discussed above, a mandatory mode of ventilation delivers mandatory breaths to a patient based on a set respiratory rate. During a mandatory mode of ventilation, the patent cannot influence when inspiration or exhalation occurs.

In some embodiments, method 500 includes a time period determination operation 504. The ventilator during time period determination operation 504 determines if a time period has expired. The time period begins with the start of the mandatory mode of ventilation. The start of the mandatory mode of ventilation is any time the ventilator is switched into a mandatory mode of ventilation from a different mode of ventilation or at the beginning of ventilation just after the ventilator is turned on. In some embodiments, the time period is about 30 minutes, 45 minutes, 60 minutes, 75 minutes, 90 minutes, 105 minutes, or 120 minutes. The time period may be any suitable amount of time that provides the spontaneous mode often enough to the patient to prevent or mitigate diaphragm atrophy or weakness. The time period may be determined by the operator or predetermined by the ventilator. If the ventilator determines during the time period determination operation 504 that the time period has expired, the ventilator selects to perform a spontaneous mode operation 506. If the ventilator determines during time period determination operation 504 that the time period has not expired, the ventilator selects to continue to perform the time period determination operation 504.

In other embodiments, the ventilator during method 500 switches from the mandatory mode to the spontaneous mode after a specific event, such as a predetermined number of breaths, inspirations, or cycles. In further embodiments, the ventilator during method 500 switches from the mandatory mode to the spontaneous mode based on clinician input or selection.

Further, method 500 includes a spontaneous mode operation 506. The ventilator during the spontaneous mode operation 506 ventilates the patient based on a spontaneous mode of operation. In some embodiments, the breath type delivered during the spontaneous mode is selected or input by an operator. In other embodiments, the breath type delivered during the spontaneous mode is determined by the ventilator. Several different breath types may be utilized during the spontaneous mode. For example, a CPAP, Bilevel, VS, PS, PA, or TC breath type may be utilized during the spontaneous mode. As discussed above, during a spontaneous mode of ventilation, inspiration and/or exhalation is delivered upon the detection of inspiratory and/or expiratory effort by the patient based on a trigger type. However, for safety measures, inspiration and exhalation may be delivered after a predetermined amount of time passes to insure that the patient receives breathing gas in the event the patient stops making inspiratory and/or expiratory patient efforts. The spontaneous mode operation 506 is performed by the ventilator until the first of several events occur, which are determined in an event determination operation 508. Accordingly, the ventilator performs the event determination operation 508 while performing the spontaneous mode operation 506. Accordingly, the event determination operation 508 and the spontaneous mode operation 506 may be performed simultaneously.

Further, in some embodiments, during the spontaneous mode operation 506, the ventilator automatically increases a fractionally inspired oxygen ($FiO_2$) and/or positive end expiratory pressure (PEEP) delivered to the patient during the exercise period. Alternatively, during the spontaneous mode operation 506, the ventilator in some embodiments, monitors $SpO_2$. During this embodiment, the ventilator during the spontaneous mode operation 506 determines if the monitored $SpO_2$ dropped during the exercise period. Based on this determination, the ventilator during the spontaneous mode operation 506 may increase the amount of oxygen delivered to the patient.

If the ventilator during the spontaneous mode operation 506 determines that the $SpO_2$ dropped during the exercise period, then the ventilator delivers more oxygen to the patient. If the ventilator during the spontaneous mode operation 506 determines that the $SpO_2$ does not drop during the exercise period, then the ventilator does not change the amount of oxygen delivered to the patient. The ventilator does not change the amount of oxygen delivered to the patient because the amount of oxygen the patient is receiving is sufficient for ventilating the patient. In some embodiments, the ventilator 100 during the spontaneous mode operation 506 increases the level of $FiO_2$ delivered to the by about 5%.

As illustrated, method 500 includes an event determination operation 508. The ventilator during the event determination operation 508 monitors for the occurrence of an event. If ventilator determines that an event occurred during event determination operation 508, the ventilator selects to perform mandatory mode operation 502. Accordingly, the ventilator during the mandatory mode operation 502 delivers the previously set mandatory mode of operation to the patient. If the ventilator does not determine an occurrence of an event during event determination operation 508, the ventilator selects to continue to perform spontaneous mode operation 506.

The ventilator during the event determination operation 508 monitors for an occurrence of one or more events. As soon as the ventilator during the event determination operation 508 determines that one event of a plurality of event occurs, the ventilator selects to perform mandatory mode operation 502. In other words, the ventilator selects to perform mandatory mode operation 502 based on the first of any of the plurality of events to occur.

In some embodiments, the event is the detection of patient fatigue. The patient fatigue may be detected by the ventilator based on method 200 as described above. In some embodiments, at least one of the fatigue indicators utilized by method 200 to detect fatigue during method 500 is WOB.

In additional embodiments the event is the detection of a trend towards patient fatigue. The detection of a trend toward patient fatigue is determined by the ventilator when two or more consecutive changes from the baseline in a fatigue indicator are detected that do not breach the fatigue threshold but get consecutively closer to breaching the fatigue threshold.

In other embodiments, the event is the expiration of an exercise period. The predetermined exercise period begins at the start of spontaneous ventilation. In some embodiments the predetermined exercise period is determined by the ventilator. In other embodiments, the predetermined exercise period is selected or input by a clinician. In some embodiments, the predetermined exercise period is about 1 minute, 2 minutes, 3 minutes, 4 minutes, 5 minutes, 6 minutes, 7 minutes, 8 minutes, 9 minutes, or 10 minutes. However, the predetermined exercise time may be any suitable time frame for providing the patent with an opportunity to spontaneously trigger a breath to provide the diaphragm of the patient with some exercise. However, the exercise period should not be so long that the exercise period deprives a non-triggering patient with necessary ventilation.

In further embodiments, the event is the expiration of an exercise period during which no inspiration triggers are detected. In this embodiment, if a trigger is detected, the ventilator continues to ventilate the patient in the spontaneous mode of ventilation until patient fatigue is detected or until no triggers are detected for an entire duration of the set exercise period. In this embodiment, every time a trigger is detected, the exercise period starts over until a trigger is not detected for the entire exercise period. Accordingly, in this embodiment, if the patient continues to trigger and does not get fatigued, the patient could be ventilated in the spontaneous mode until removed from the ventilator or until a clinician switches the mode of ventilation. There are several different trigger types or systems and/or methods utilized by the ventilator for detecting patient triggers and/or cycles. In some embodiments, the trigger type for detecting patient effort may be selected or input by an operator. In some embodiments, the trigger type is automatically selected by the ventilator. Any suitable type of triggering detection for determining a patient trigger may be utilized by the ventilator, such as nasal detection, diaphragm detection, and/or brain signal detection. Further, the ventilator may detect patient triggering via a pressure-monitoring method, a flow-monitoring method, direct or indirect measurement of neuromuscular signals, or any other suitable method, which are described in more detail above. Sensors suitable for this detection may include any suitable sensing device as known by a person of skill in the art for a ventilator. In addition, the sensitivity of the ventilator to changes in pressure and/or flow may be adjusted such that the ventilator may properly detect the patient effort, i.e., the lower the pressure or flow change setting the more sensitive the ventilator may be to patient triggering.

In some embodiments, method 500 includes a displaying operation. The ventilator during the displaying operation displays one or more notifications relating to the time period, exercise period, detected triggers, oxygen threshold, mode of ventilation, breath type, detected fatigue, monitored $FiO_2$, monitored PEEP, and/or any other parameter relating to the exercise of the diaphragm. For example, the notification may display that the time period is active, that the exercise period is being utilized, and/or a change to the delivered oxygen. These notifications include any of the features discussed above for a notification message, such as a hierarchical structure, display on a remote monitoring system, and/or a summarize format with recommendations offered upon selection.

For example, the ventilator during displaying operation may notify the clinician by displaying a notification on a display and/or within a window of the GUI. According to additional embodiments, the notification is communicated to and/or displayed on a remote monitoring system. According to alternative embodiments, the notification is any audio and/or visual notification.

In additional embodiments, if the event determination operation 508 detects patient fatigue, method 500 further confirms the detected fatigue. The confirming operation performed by method 500 is identical to confirming operation 218 as illustrated in FIG. 3C and FIG. 4 and as described above. However, the changing breath type operation 216 is specific to changing from a spontaneous mode breath type delivered by the ventilator during the spontaneous mode operation 506 to a mandatory mode breath type utilized in the set mandatory mode as was previously utilized by the ventilation during mandatory mode operation 502 of method 500.

In some embodiments, the displaying operation of method 500 is performed after the confirming step. The ventilator after determining that patient fatigue is mitigated, displays a fatigue mitigation notification message as described above for method 200 and as illustrated in FIG. 3C. The ventilator after determining that the patient fatigue is unmitigated, displays an unmitigated patient event notification message as described above for method 200 and as illustrated in FIG. 3C. The notification displayed by the displaying operation 212 is similar to the notification described above and therefore may exhibit any of the features described above for a notification message, such as a hierarchical structure, display on a remote monitoring system, and/or a summarize format with recommendations offered upon selection.

In some embodiments, a patient's diaphragm may develop weakness during an assist/control mode, because the ventilator may still be performing the bulk of the work for the patient during ventilation. Accordingly, method 500 may be performed according to the disclosure listed above except that the mandatory mode of ventilator is replaced with the assist/control mode of ventilation.

In some embodiments, a microprocessor-based ventilator that accesses a computer-readable medium having computer-executable instructions for performing the method of ventilating a patient with a ventilator is disclosed. This method includes repeatedly performing the steps disclosed in method 500 above and/or as illustrated in FIG. 5

In some embodiments, the ventilator system includes: means for ventilating a patient based on a set mandatory mode of ventilation; means for switching from the mandatory mode of ventilation to the spontaneous mode of ventilation to ventilate the patient until the first of the following events occur: 1) detection of patient fatigue, and 2) no inspiratory triggers are detected and expiration of a predetermined exercise period; and upon occurrence of the event, means for ventilating the patient based on the set mandatory mode of ventilation.

In some embodiments, the ventilator system includes: means for ventilating a patient based on a set mandatory mode of ventilation; means for switching from the mandatory mode of ventilation to the spontaneous mode of ventilation to ventilate the patient until the first of the following events occur: 1) detection of patient fatigue, and 2) expiration of a predetermined exercise period; and upon occurrence of the event, means for ventilating the patient based on the set mandatory mode of ventilation.

Those skilled in the art will recognize that the methods and systems of the present disclosure may be implemented in many manners and as such are not to be limited by the foregoing exemplary embodiments and examples. In other words, functional elements being performed by a single or multiple components, in various combinations of hardware and software or firmware, and individual functions, can be distributed among software applications at either the client or server level or both. In this regard, any number of the features of the different embodiments described herein may be combined into single or multiple embodiments, and alternate embodiments having fewer than or more than all of the features herein described are possible. Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, and those variations and modifications that may be made to the hardware or software firmware components described herein as would be understood by those skilled in the art now and hereafter.

Numerous other changes may be made which will readily suggest themselves to those skilled in the art and which are encompassed in the spirit of the disclosure and as defined in the appended claims. While various embodiments have been described for purposes of this disclosure, various changes and modifications may be made which are well within the scope of the present invention. Numerous other changes may be made which will readily suggest themselves to those skilled in the art and which are encompassed in the spirit of the disclosure and as defined in the appended claims.

What is claimed is:

1. A method for ventilating a patient with a ventilator comprising:
   ventilating the patient based on a set mandatory mode of ventilation;
   switching from the set mandatory mode of ventilation to ventilate the patient based on a spontaneous mode of ventilation;
   monitoring at least one fatigue indicator during the spontaneous mode;
   establishing a baseline for the at least one fatigue indicator during the spontaneous mode;
   determining a change from the baseline based on the monitored at least one fatigue indicator during the spontaneous mode;
   comparing the change to a corresponding fatigue threshold during the spontaneous mode;
   detecting respiratory fatigue based on the step of comparing the change to the corresponding fatigue threshold during the spontaneous mode;
   switching from the spontaneous mode of ventilation back to the set mandatory mode of ventilation in response to detecting respiratory fatigue; and
   displaying a fatigue notification in response to detecting respiratory fatigue.

2. The method of claim 1, wherein the step of detecting respiratory fatigue comprises:
   determining that the change breaches the corresponding fatigue threshold.

3. The method of claim 1, wherein the fatigue notification includes at least one of the following notifications:
   fatigue detection;
   level of fatigue;
   fatigue index;
   the corresponding fatigue threshold;
   fatigue detected;
   fatigue implicated;

fatigue warning; and
notice of fatigue.

4. The method of claim 1, wherein the fatigue notification includes a message.

5. The method of claim 1, wherein the spontaneous mode of ventilation is a positive feedback breath type.

6. The method of claim 1, further comprising:
monitoring for a rested fatigue indicator after a predetermined rest time,
wherein the predetermined rest time begins when the step of switching from the spontaneous mode of ventilation back to the set mandatory mode of ventilation is performed;
comparing the rested fatigue indicator to the baseline;
determining that the detected respiratory fatigue was mitigated by switching from the spontaneous mode of ventilation back to the set mandatory mode of ventilation based on the step of comparing the rested fatigue indicator to the baseline.

7. The method of claim 1, wherein the spontaneous mode of ventilation utilizes a breath type selected from a group of a proportional assist (PA) breath type and diaphragmatic electromyography adjusted (DEA) breath type; and
wherein the set mandatory mode of ventilation utilizes a non-positive feedback breath type.

8. The method of claim 1, wherein the step of establishing the baseline includes receiving the baseline from clinician input.

9. The method of claim 1, wherein the monitored at least one fatigue indicator and the corresponding fatigue threshold are selected from a group comprising:
work of breathing decrease below the baseline,
the work of breathing increases above the baseline followed by a decrease below the baseline,
$PaCO_2$ increases by at least 10 mmHg from the baseline,
$VCO_2$ decreases by more than 20% from the baseline,
EMG of an accessory muscle indicates use of the accessory muscle,
$E_{di}$ decreases by at least 25% from the baseline,
$E_{di}$ stays the same while velocity of muscle shortening decreases below the baseline,
$P_{di}$ decreases by at least 10% from the baseline,
$P_{di,max}$ decreases by at least 20% from the baseline,
$P_{i,max}$ decreases by at least 20% from the baseline,
a velocity of muscle shortening decreases at least 25% from the baseline,
EMG time domain is less than 50 uV,
EMG frequency domain decreases by more than 20% from the baseline,
$P_{esoph}$ decreases by at least 10% from the baseline,
$P_{di}$ Maximum Relaxation Rate decreases by at least 20% from the baseline,
$P_{mus}$ Maximum Relaxation Rate decreases by at least 20% from the baseline,
presence of paradoxical breathing,
$V_{e\;alv}$ decreases by at least 20% from the baseline,
respiration rate increases above 35 breaths a minute,
respiration rate increases by at least 25% from the baseline followed by a decrease,
$V_t/T_i$ decreases by 30% from the baseline,
$V_d/V_t$ increases by 20% from the baseline,
$V_d/V_t$ is greater than 40% from the baseline,
$P_{0.1}$ increases above 4 cm of $H_2O$ and then decreases by at least 2 cm of $H_2O$,
diaphragmatic position becomes flattened,
cardiac output does not increase with an increasing load,
$V_t$ is below 4 mL/kg,
diaphragm movement imaging shows reduced movement compared to the baseline,
alternating abdominal/rib cage muscle contractions occur or increase in frequency compared to the baseline,
BIS LOS is normal,
RSBI increases above 105,
$P_{di}/P_{di\;max}$ is above 40%,
$T_i/T_{tot}$ is greater than 40%,
$P_{tid}$ increases above 0.15,
$T_i/T_{tot}/P_{di}/P_{dimax}$ is greater than 40%,
$E_{di}$ increases while $E_{phr}$ increases and $P_{di}$ decreases,
the $P_{di,max}$ increases from the baseline,
the $P_{i,max}$ increases from the baseline,
$E_{di}$ increases from the baseline and at least one of a decrease in $V_t$, a decrease in $VCO_2$, a decrease in $SpO_2$, an increase in $P_{at}$, and a decrease in MV occurs, and
$P_{mus}$ decreases from the baseline and at least one of a decrease in $V_t$, a decrease in $VCO_2$, a decrease in $SpO_2$, and a decrease in MV occurs.

10. The method of claim 1, wherein the step of establishing the baseline includes averaging a set of measurements for each of the monitored fatigued indicators for a predetermined amount of time.

11. A ventilator system comprising:
a pressure generating system adapted to generate a flow of breathing gas according to a mode of ventilation, wherein the mode of ventilation is a mandatory mode of ventilation;
a ventilation tubing system including a patient interface for connecting the pressure generating system to a patient;
a plurality of sensors operatively coupled to at least one of the pressure generating system, the patient, and the ventilation tubing system, wherein the plurality of sensors monitor a plurality of parameters to generate sensor output;
a switch module sending instructions to the pressure generating system to switch from the mandatory mode of ventilation to a spontaneous mode of ventilation;
a baseline module determines a baseline for at least one fatigue indicator and determines a change in the at least one fatigue indicator from the baseline based on the sensor output during the spontaneous mode of ventilation;
a fatigue module compares the change to a corresponding fatigue threshold and determines that the patient is fatigued based on the comparison during the spontaneous mode of ventilation, wherein the switch module sends instructions to the pressure generating system to switch back to the mandatory mode of ventilation in response to determining that the patient is fatigued by the fatigue module;
a notification module determines an appropriate notification; and
a graphical user interface displays the appropriate notification received from the notification module, wherein the appropriate notification notifies a clinician that the fatigue module determined that the patient is fatigued.

12. The ventilator system of claim 11, wherein the fatigue module determines that the change breached the corresponding fatigue threshold.

13. The ventilator system of claim 11, further comprising:
an indicator module, wherein the indicator module derives the at least one fatigue indicator from the sensor output.

14. The ventilator system of claim 11, wherein the at least one fatigue indicator and the corresponding fatigue threshold are selected from a group comprising:
    work of breathing decrease below the baseline,
    the work of breathing increases above the baseline followed by a decrease below the baseline,
    $PaCO_2$ increases by at least 10 mmHg from the baseline,
    $VCO_2$ decreases by more than 20% from the baseline,
    EMG of an accessory muscle indicates use of the accessory muscle,
    $E_{di}$ decreases by at least 25% from the baseline,
    $E_{di}$ stays the same while velocity of muscle shortening decreases below the baseline,
    $P_{di}$ decreases by at least 10% from the baseline,
    $P_{di,max}$ decreases by at least 20% from the baseline,
    $P_{i,max}$ decreases by at least 20% from the baseline,
    a velocity of muscle shortening decreases at least 25% from the baseline,
    EMG time domain is less than 50 uV,
    EMG frequency domain decreases by more than 20% from the baseline,
    $P_{esoph}$ decreases by at least 10% from the baseline,
    $P_{di}$ Maximum Relaxation Rate decreases by at least 20% from the baseline,
    $P_{mus}$ Maximum Relaxation Rate decreases by at least 20% from the baseline,
    presence of paradoxical breathing,
    $V_{e\ alv}$ decreases by at least 20% from the baseline,
    respiration rate increases above 35 breaths a minute,
    respiration rate increases by at least 25% from the baseline followed by a decrease,
    $V_t/T_i$ decreases by 30% from the baseline,
    $V_d/V_t$ increases by 20% from the baseline,
    $V_d/V_t$ is greater than 40% from the baseline,
    $P_{0.1}$ increases above 4 cm of $H_2O$ and then decreases by at least 2 cm of $H_2O$,
    diaphragmatic position becomes flattened,
    cardiac output does not increase with an increasing load,
    $V_t$ is below 4 mL/kg,
    diaphragm movement imaging shows reduced movement compared to the baseline,
    alternating abdominal/rib cage muscle contractions occur or increase in frequency compared to the baseline,
    BIS LOS is normal,
    RSBI increases above 105,
    $P_{di}/P_{di\ max}$ is above 40%,
    $T_i/T_{tot}$ is greater than 40%,
    $P_{tid}$ increases above 0.15,
    $T_i/T_{tot}/P_{di}/P_{dimax}$ is greater than 40%,
    $E_{di}$ increases while $E_{phr}$ increases and $P_{di}$ decreases,
    the $P_{di,max}$ increases from the baseline,
    the $P_{i,max}$ increases from the baseline,
    $E_{di}$ increases from the baseline and at least one of a decrease in $V_t$, a decrease in $VCO_2$, a decrease in $SpO_2$, an increase in $P_{0.1}$, and a decrease in MV occurs, and
    $P_{mus}$ decreases from the baseline and at least one of a decrease in $V_t$, a decrease in $VCO_2$, a decrease in $SpO_2$, and a decrease in MV occurs.

15. A computer-readable medium having computer-executable instructions for performing a method of ventilating a patient with a ventilator, the method comprising:
    delivering ventilation based on a positive feedback breath type;
    monitoring output from at least one sensor;
    monitoring a plurality of fatigue indicators based on the output;
    establishing a baseline for at least one fatigue indicator based on the output;
    determining a change from the baseline based on the monitored plurality of fatigue indicators;
    comparing the change to a fatigue threshold;
    detecting respiratory fatigue based on the step of comparing the change to the fatigue threshold by the ventilator;
    displaying a fatigue notification after the step of detecting respiratory fatigue;
    implementing a basal level of support for the positive feedback breath type after the step of detecting respiratory fatigue;
    monitoring for a rested fatigue indicator after a predetermined rest time, wherein the predetermined rest time begins when the step of implementing the basal level of support is performed;
    comparing the rested fatigue indicator to the baseline; and
    determining that the detected respiratory fatigue was mitigated by the step of implementing the basal level of support based on the step of comparing the rested fatigue indicator to the baseline.

16. A method for ventilating a patient with a ventilator comprising:
    monitoring a plurality of fatigue indicators;
    establishing a baseline for the plurality of fatigue indicators by averaging a set of measurements for each indicator in the plurality of fatigued indicators for a predetermined amount of time;
    determining a change from the baseline based on the monitored fatigue indicators;
    comparing the change to a corresponding fatigue threshold;
    detecting respiratory fatigue based on the step of comparing the change to the fatigue threshold;
    displaying a fatigue notification after the step of detecting respiratory fatigue;
    switching from a spontaneous mode of ventilation to a mandatory mode of ventilation in response to the detecting respiratory fatigue; and
    determining that the detected respiratory fatigue was mitigated by the step of switching to the mandatory mode of ventilation.

17. The method of claim 16, wherein the step of detecting respiratory fatigue comprises:
    determining that the change breaches the fatigue threshold.

18. The method of claim 16, wherein the fatigue notification includes at least one of the following notifications:
    fatigue detection;
    level of fatigue;
    fatigue index;
    the fatigue threshold;
    fatigue detected;
    fatigue implicated;
    fatigue warning; and
    notice of fatigue.

19. The method of claim 16, further comprising:
    ventilating the patient based on the mandatory mode of ventilation;
    switching from the mandatory mode of ventilation to the spontaneous mode of ventilation,
    wherein the monitoring the plurality of fatigue indicators, the establishing the baseline for the plurality of fatigue indicators, the determining the change from the baseline based on the monitored fatigue indicators, the comparing the change to the corresponding fatigue threshold, and the detecting respiratory fatigue are all performed during the spontaneous mode of ventilation.

20. The method of claim 16, wherein the fatigue notification includes a message.

21. The method of claim 20, wherein the message is selected from a group of the following messages:
consider switching to invasive ventilation;
consider switching to a negative feedback breath type;
consider switching to a PS, PC, VC, or VS breath type;
consider increasing support setting in a PA breath type;
consider increasing support setting in a DEA breath type;
consider increasing support setting in a positive feedback breath type;
consider increasing set respiratory rate;
consider utilizing a basal level of support in the PA breath type;
consider utilizing a basal level of support in the DEA breath type; and
consider utilizing a basal level of support in the positive feedback breath type.

22. The method of claim 16, further comprising:
delivering ventilation based on a positive feedback breath type;
implementing a basal level of support for the positive feedback breath type after the step of detecting respiratory fatigue.

23. The method of claim 22, wherein the basal level of support is at least 5 cmH$_2$O.

24. The method of claim 22, further comprising:
monitoring for a rested fatigue indicator after a predetermined rest time, wherein the predetermined rest time begins the step of implementing the basal level of support is performed;
comparing the rested fatigue indicator to the baseline;
determining that the detected respiratory fatigue was mitigated by step of implementing the basal level of support based on the step of comparing the rested fatigue indicator to the baseline.

25. The method of claim 16, further comprising:
delivering ventilation based on a breath type selected from a group of a proportional assist (PA) breath type and diaphragmatic electromyography adjusted (DEA) breath type; and
delivering ventilation based on a non-positive feedback breath type after the step of detecting respiratory fatigue.

26. The method of claim 16, wherein the monitored at least one fatigue indicator and the corresponding fatigue threshold are selected from a group comprising:
work of breathing decrease below the baseline,
the work of breathing increases above the baseline followed by a decrease below the baseline,
PaCO$_2$ increases by at least 10 mmHg from the baseline,
VCO$_2$ decreases by more than 20% from the baseline,
EMG of an accessory muscle indicates use of the accessory muscle,
E$_{di}$ decreases by at least 25% from the baseline,
E$_{di}$ stays the same while velocity of muscle shortening decreases below the baseline,
P$_{di}$ decreases by at least 10% from the baseline,
P$_{di,max}$ decreases by at least 20% from the baseline,
P$_{i,max}$ decreases by at least 20% from the baseline,
a velocity of muscle shortening decreases at least 25% from the baseline,
EMG time domain is less than 50 uV,
EMG frequency domain decreases by more than 20% from the baseline,
P$_{esoph}$ decreases by at least 10% from the baseline,
P$_{di}$ Maximum Relaxation Rate decreases by at least 20% from the baseline,
P$_{mus}$ Maximum Relaxation Rate decreases by at least 20% from the baseline,
presence of paradoxical breathing,
V$_{e\ alv}$ decreases by at least 20% from the baseline,
respiration rate increases above 35 breaths a minute,
respiration rate increases by at least 25% from the baseline followed by a decrease,
V$_t$/T$_i$ decreases by 30% from the baseline,
V$_d$/V$_t$ increases by 20% from the baseline,
V$_d$/V$_t$ is greater than 40% from the baseline,
P$_{0.1}$ increases above 4 cm of H$_2$O and then decreases by at least 2 cm of H$_2$O,
diaphragmatic position becomes flattened,
cardiac output does not increase with an increasing load,
V$_t$ is below 4 mL/kg,
diaphragm movement imaging shows reduced movement compared to the baseline,
alternating abdominal/rib cage muscle contractions occur or increase in frequency compared to the baseline,
BIS LOS is normal,
RSBI increases above 105,
P$_{di}$/P$_{di\ max}$ is above 40%,
T$_i$/T$_{tot}$ is greater than 40%,
P$_{tid}$ increases above 0.15,
T$_i$/T$_{tot}$/P$_{di}$/P$_{dimax}$ is greater than 40%,
E$_{di}$ increases while E$_{phr}$ increases and P$_{di}$ decreases,
the P$_{di,max}$ increases from the baseline,
the P$_{i,max}$ increases from the baseline,
E$_{di}$ increases from the baseline and at least one of a decrease in V$_t$, a decrease in VCO$_2$, a decrease in SpO$_2$, an increase in P$_{at}$, and a decrease in MV occurs, and
P$_{mus}$ decreases from the baseline and at least one of a decrease in V$_t$, a decrease in VCO$_2$, a decrease in SpO$_2$, and a decrease in MV occurs.

27. A ventilator system comprising:
a pressure generating system adapted to generate a flow of breathing gas;
a ventilation tubing system including a patient interface for connecting the pressure generating system to a patient;
a plurality of sensors operatively coupled to at least one of the pressure generating system, the patient, and the ventilation tubing system, wherein the plurality of sensors monitor a plurality of parameters to generate sensor output;
a baseline module determines a baseline for at least one fatigue indicator and determines a change in the at least one fatigue indicator from the baseline based on the sensor output;
a fatigue module compares the change to a corresponding fatigue threshold and determines that the patient is fatigued based on the comparison,
wherein the fatigue module after determining that the patient is fatigued instructs the pressure generating system to deliver a baseline level of support for a predetermined rest time,
wherein the fatigue module after the predetermined rest time determines a rested fatigue indicator based on the sensor output, and
wherein the fatigue module compares the rested fatigue indicator to the baseline and confirms that the patient was fatigued based on the comparison of the rested fatigue indicator to the baseline;
a notification module determines an appropriate notification; and
a graphical user interface displays the appropriate notification received from the notification module, wherein the appropriate notification notifies a clinician that the fatigue module determined that the patient is fatigued.

* * * * *